United States Patent [19]

Schwede et al.

[11] Patent Number: 5,426,102
[45] Date of Patent: Jun. 20, 1995

[54] 14β-H-, 14- AND 15-EN-11β-ARYL-4-OESTRENES

[75] Inventors: Wolfgang Schwede; Eckhard Ottow; Günter Neef; Arwed Cleve; Krzysztof Chwalisz; Horst Michna, all of Berlin, Germany

[73] Assignee: Schering Aktiengesellschaft, Berlin and Bergkamen, Germany

[21] Appl. No.: 81,269

[22] PCT Filed: Dec. 21, 1991

[86] PCT No.: PCT/EP91/02494

§ 371 Date: Jun. 22, 1993

§ 102(e) Date: Nov. 1, 1993

[87] PCT Pub. No.: WO92/11278

PCT Pub. Date: Jul. 9, 1992

[30] Foreign Application Priority Data

Dec. 22, 1990 [DE] Germany .................. 40 42 004.3

[51] Int. Cl.⁶ .................. C07J 7/00; C07J 21/00; C07J 41/00; C07J 43/00
[52] U.S. Cl. .................. 514/173; 514/175; 514/176; 514/178; 514/181; 514/182; 540/28; 540/41; 540/44; 540/106; 540/107; 540/108; 552/520; 552/540; 552/548; 552/553; 552/554; 552/593; 552/598; 552/610; 552/646; 552/648
[58] Field of Search .................. 540/44, 106, 107, 108, 540/28, 41; 514/175, 176, 178, 181, 182, 173; 552/520, 540, 548, 553, 554, 593, 598, 610, 646, 648

[56] References Cited

U.S. PATENT DOCUMENTS

| 4,477,445 | 10/1984 | Philibert et al. | 424/239 |
|---|---|---|---|
| 4,540,686 | 9/1985 | Philibert et al. | 514/179 |
| 4,780,461 | 10/1988 | Neef et al. | 514/179 |
| 4,814,327 | 3/1989 | Ottow et al. | 514/179 |
| 4,829,060 | 5/1989 | Ottow et al. | 514/179 |
| 4,954,490 | 9/1990 | Cook et al. | 514/176 |
| 5,006,518 | 4/1991 | Moguilewsky | 514/179 |
| 5,073,548 | 12/1991 | Cook et al. | 514/169 |
| 5,244,886 | 9/1993 | Scholz et al. | 514/175 |
| 5,272,140 | 12/1993 | Loozen | 514/172 |
| 5,273,971 | 12/1993 | Scholz et al. | 514/176 |

FOREIGN PATENT DOCUMENTS 0299913 1/1989 European Pat. Off. .
0360369 3/1990 European Pat. Off. .

Primary Examiner—Howard T. Mars
Assistant Examiner—Kimberly J. Kestler
Attorney, Agent, or Firm—Millen, White, Zelano, & Branigan

[57] ABSTRACT

Novel compounds of the general formula I

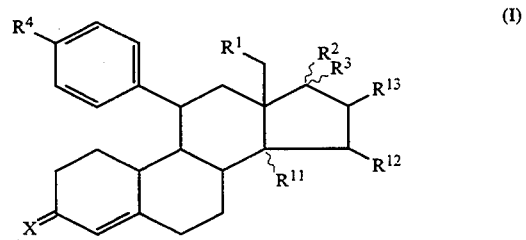

and the pharmacologically tolerable addition salts thereof with acids are described, in which either Ia) $R^{11}$ represents a hydrogen atom in the β-configuration and each of $R^{12}$ and $R^{13}$ represents a hydrogen atom, or Ib) $R^{11}$ represents a hydrogen atom in the β-configuration and $R^{12}$ and $R^{13}$ together represent a second bond, or Ic) $R^{11}$ and $R^{12}$ together represent a second bond and $R^{13}$ represents a hydrogen atom, or Id) $R^{11}$ represents a hydrogen atom in the α-configuration and $R^{12}$ and $R^{13}$ together represent a second bond, and in Ia), Ib), Ic) or Id)

X represents an oxygen atom, the hydroxyimino grouping >N~OH or two hydrogen atoms, $R^1$ represents a hydrogen atom or a methyl group, $R^2$ represents a hydroxy group, a $C_1$-$C_{10}$-alkoxy group or a $C_1$-$C_{10}$-acyloxy group, and $R^3$ and $R^4$ have the meanings customary for competi- (Abstract continued on next page.)

tive progesterone antagonists specified in the description.

The invention relates also to processes for the preparation of the novel compounds, to pharmaceutical compositions containing those compounds, to their use for the manufacture of medicaments, and to the novel intermediates required for the process.

The novel compounds have a strong affinity for the gestagen receptor and exhibit pronounced antigestagenic and also antiglucocorticoid, antimineralocorticoid and antiandrogenic properties.

3 Claims, No Drawings

14β-H-, 14-AND 15-EN-11β-ARYL-4-OESTRENES

The present invention relates to compounds of the general formula I

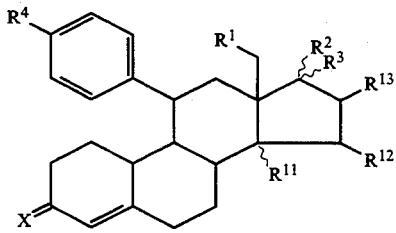

in which either

Ia) $R^{11}$ represents a hydrogen atom in the β-configuration and each of $R^{12}$ and $R^{13}$ represents a hydrogen atom, or Ib) $R^{11}$ represents a hydrogen atom in the β-configuration and $R^{12}$ and $R^{13}$ together represent a second bond, or Ic) $R^{11}$ and $R^{12}$ together represent a second bond and $R^{13}$ represents a hydrogen atom, or Id) $R^{11}$ represents a hydrogen atom in the α-configuration and $R^{12}$ and $R^{13}$ together represent a second bond, and in Ia), Ib), Ic) or Id)

X represents an oxygen atom, the hydroxyimino grouping >N~OH or two hydrogen atoms, $R^1$ represents a hydrogen atom or a methyl group, $R^2$ represents a hydroxy group, a $C_1$-$C_{10}$-alkoxy group or a $C_1$-$C_{10}$-acyloxy group, $R^3$ represents a hydrogen atom; the grouping —$(CH_2)_nCH_2Z$ wherein n is 0, 1, 2, 3, 4 or 5 and Z represents a hydrogen atom, a cyano group or the radical —$OR^5$ in which $R^5$=H, $C_1$-$C_{10}$-alkyl or $C_1$-$C_{10}$-acyl; the grouping —$(CH_2)_mC\equiv C$—Y wherein m is 0, 1 or 2 and Y represents a hydrogen, fluorine, chlorine, bromine or iodine atom, or a $C_1$-$C_{10}$-hydroxyalkyl, $C_1$-$C_{10}$-alkoxyalkyl or $C_1$-$C_{10}$-acyloxyalkyl radical; or the grouping —$(CH_2)_p$—CH=CH—$(CH_2)_k CH_2 R^6$ wherein p is 0 or 1 and k is 0, 1 or 2 and $R^6$ represents a hydrogen atom, a hydroxy group, a $C_1$-$C_4$-alkoxy radical or a $C_1$-$C_4$-acyloxy radical, wherein in Ia) and Ib) $R^2$ is in the α-configuration and $R^3$ is in the β-configuration and in Ic) and Id) $R^2$ is in the β-configuration and $R^3$ is in the α-configuration, or alternatively $R^2$ and $R^3$ together represent a radical of the formula

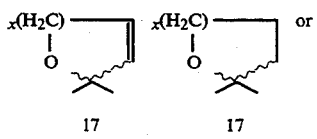

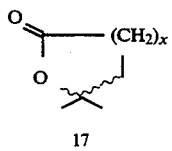

wherein x=1 or 2, $R^4$ represents a hydrogen atom; a cyano group; a chlorine, fluorine, bromine or iodine atom; a trialkylsily group; a trialkylstannyl group; a straight-chain or branched, saturated or unsaturated, $C_1$-$C_8$-alkyl, -acyl or alkoxyalkyl radical; an amino group

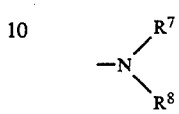

in which $R^7$ and $R^8$, each independently of the other, represents a hydrogen atom or a $C_1$-$C_4$-alkyl group; a corresponding amine oxide

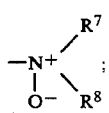

or the grouping —$OR^9$ or —$S(O)_i R^9$ in which i=0, 1 or 2 and $R^9$ represents a hydrogen atom, a methyl, ethyl, propyl, isopropyl, methoxyphenyl, allyl or 2-dimethylaminoethyl group; or $R^4$ represents a heteroaryl radical of formula Iα

in which A represents a nitrogen, oxygen or sulphur atom, —B—D—E— represents the sequence of elements —C—C—C—, —N—C—C— or —C—N—C— and $R^{10}$ represents a hydrogen atom; a cyano group; a chlorine, fluorine, bromine or iodine atom; a trialkylsilyl group; a trialkylstannyl group; a straight-chain or branched, saturated or unsaturated $C_1$-$C_8$-alkyl, -acyl or alkoxyalkyl radical; an amino group

in which $R^7$ and $R^8$, each independently of the other, represents a hydrogen atom or a $C_1$-$C_4$-alkyl group; a corresponding amine oxide

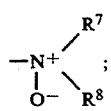

or the grouping —$OR^9$ or —$S(O)_i R^9$ in which i=0, 1 or 2 and $R^9$ represents a hydrogen atom, a methyl, ethyl, propyl, isopropyl, methoxyphenyl, allyl or 2-dimethylaminoethyl group; or $R^4$ represents a heteroaryl radical of formula Iβ

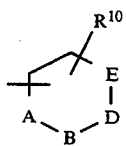 (Iβ)

in which A represents a nitrogen atom and —B—D—E— represents the sequence of elements —C—C—C—, —N—C—C—, —C—N—C— or —C—C—N— and $R^{10}$ has the meaning already given, or $R^4$ represents a phenyl radical of formula Iγ

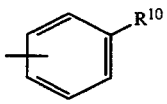 (Iγ)

in which $R^{10}$ has the meaning already given, and the pharmacologically tolerable addition salts thereof with acids, to processes for their preparation, to pharmaceutical compositions containing those compounds, to their use for the manufacture of medicaments, and to the novel intermediates required therefor.

The invention relates especially to compounds in which X represents an oxygen atom.

The alkoxy, acyloxy, alkyl, acyl and hydroxyalkyl groups contained in $R^2$, $R^3$, $R^5$ and Y in the general formula I shall each have from 1 to 10 carbon atoms, and the alkoxyalkyl or acyloxyalkyl groups in Y shall each have from 2 to 10 carbon atoms. There may be mentioned as preferred alkoxy groups methoxy, ethoxy, propoxy and isopropoxy groups, and of the acyl(oxy) groups, formyl(oxy), acetyl(oxy) and propionyl(oxy) are of particular importance.

The alkyl groups are especially methyl, ethyl, propyl, isopropyl and tert.-butyl groups and, of the hydroxyalkyl groups, the corresponding radicals substituted at any position by a hydroxy group are preferred.

There comes into consideration for n especially 0, 1, 2 or 3; when Z=CN, a cyanomethyl group (n=0) is especially preferred. In addition to the groups already mentioned, Y may preferably also be a hydrogen, chlorine or bromine atom.

Of the alkenyl radicals in $R^3$, propenyl and butenyl groups, which may be present in the E- or Z-configuration, are preferred, that is to say, when $R^3$ represents —(CH$_2$)$_p$—CH=CH—(CH$_2$)$_k$—CH$_2$—$R^6$ K shall preferably be 0 or 1 and p=0.

Of the alkoxy and acyloxy groups mentioned for $R^6$, which may be either straight-chain or branched, the methoxy, ethoxy, propoxy and isopropoxy, and the formyloxy, acetyloxy and propionyloxy groups, respectively, are especially preferred.

The $C_1$-$C_8$-alkyl and alkoxyalkyl radicals which $R^4$ may represent are especially the methyl, ethyl, propyl, isopropyl, cyclopentyl and cyclohexyl radical, and the alkoxymethyl or 1- or 2-alkoxyethyl groups containing the mentioned alkyl radicals; $R^4$ representing $C_1$-$C_8$-acyl is especially acetyl, propionyl or isobutyryl.

If $R^4$ represents the amino group

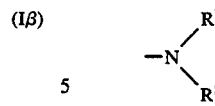

then $R^7$ and $R^8$ preferably each represent a methyl radical, or the ethyl radical is also especially important, in which case either each of the radicals at the nitrogen atom represents an ethyl radical, or one represents a methyl radical and one an ethyl radical. For the substituent $R^9$ attention is drawn especially to the methyl, ethyl and 2-(dimethylamino)-ethyl group.

Of the heteroaryl radicals possible in accordance with formula Iα, 3-thienyl, 3-furyl and 3-pyrrolyl are preferred in which $R^{10}$ represents a cyano, methoxy or dimethylamino group.

As heteroaryl radicals of formula Iβ there come into consideration in accordance with the invention especially 3- or 4-pyridyl, 5-pyrimidinyl, 4-pyridazinyl or pyrazinyl radicals. The phenyl radical of formula I γ contains as substituent $R^{10}$ especially the cyano, methoxy or dimethylamino group, these substituents preferably being in the p-position of the phenyl ring.

The following compounds are especially preferred in accordance with the invention:

17α-hydroxy-17β-(3-hydroxypropyl)-11β-[4-(3-pyridinyl)phenyl]-14β-oestr-4-en-3-one 11-β-(4-acetylphenyl)-17α-hydroxy-17β-(3-hydroxypropyl)-14β-oestr-4-en-3-one 11β-[4-(3-furanyl)phenyl]-17α-hydroxy-17β-(3-hydroxypropyl)-14β-oestr-4-en-3-one 4'-[17α-hydroxy-17β-(3-hydroxypropyl)-3-oxo-14β-oestr-4-en-11β-yl][1,1'-biphenyl]-4-carbonitrile (Z)-11β-(4-acetylphenyl)-17α-hydroxy-17β-(3-hydroxy-1-propenyl)-14β-oestr-4-en-3-one (Z)-4'-[17α-hydroxy-17β-(3-hydroxy-1-propenyl)-3-oxo-14β-oestr-4-en-11β-yl][1,1'-biphenyl]-4-carbonitrile 11β-(4-acetylphenyl)-17α-hydroxy-17β-(methoxymethyl)-14β-oestr-4-en-3-one 11β-(4-acetylphenyl)-17α-hydroxy-3-oxo-14β-oestr-4-ene-17β-acetonitrile 11β-[4-(3-furanyl)phenyl]-17α-hydroxy-17β-(3-hydroxypropyl)-14β-oestra-4,15-dien-3-one 4'-[17α-hydroxy-17β-(3-hydroxypropyl)-3-oxo-14β-oestra-4,15-dien-11β-yl][1,1'-biphenyl]-4-carbonitrile 11β-(4-acetylphenyl)-17α-hydroxy-17β-methyl-14β-oestra-4,15-dien-3-one 17β-hydroxy-11β-(4-methoxyphenyl)-17α-methyloestra-5,14-dien-3-one 11β-[4-(3-furanyl)phenyl]-17β-hydroxy-17α-methyloestra-5,14-dien-3-one 11β-(4-acetylphenyl)-17β-hydroxy-17α-methyloestra-5,14-dien-3-one 11β-(4-acetylphenyl)-17β-hydroxy-17α-(3-hydroxypropyl)oestra-5,14-dien-3-one 4'-[17β-hydroxy-17α-(3-hydroxypropyl)-3-oxo-oestra-4,14-dien-11β-yl][1,1'-biphenyl]-4-carbonitrile 11β-(4-acetylphenyl)-17β-hydroxy-17α-(1-propynyl)oestra-4,14-dien-3-one 11β-(4-acetylphenyl)-4',5'-dihydrospiro[oestra-4,14-diene-17β,2'(3'H)-furan]-3-one 11β-[4-(3-furanyl)phenyl]-17β-hydroxy-17α-(3-hydroxypropyl)oestra-4,15-dien-3-one 4'-[17β-hydroxy-17α-(3-hydroxypropyl)-3-oxo-oestra-4,15-dien-11β-yl][1,1'-biphenyl]-4-carbonitrile 11β-[4-(3-furanyl)phenyl]-17β-hydroxy-17α-methylo-
estra-4,15-dien-3-one
11β-(4-acetylphenyl)-17β-hydroxy-3-oxo-oestra-4,15-
diene-17α-acetonitrile
17-hydroxy-17α-methyl-11β-[4-(3-thienyl)phenyl]oes-
tra-4,14-dien-3-one
17β-hydroxy-11β-(4-methoxyphenyl)-17α-methyloes-
tra-4,15-dien-3-one
11β-(4-acetylphenyl)-17β-hydroxy-17α-methyoestra-
4,15-dien-3-one
17β-hydroxy-17α-methyl-11β-[4-(3-pyridinyl)phenyl-
]oestra-4,15-dien-3-one
4'-[17β-hydroxy-17α-methyl-3-oxo-oestra-4,15-dien-
11β-yl][1,1'-biphenyl]-4-carbonitrile
4'-[17β-methoxy-17α-methyl-3-oxo-oestra-4,15-dien-
11β-yl][1,1'-biphenyl]-4-carbonitrile
17β-hydroxy-11β-(4-methoxyphenyl)-17α-(1-propynyl-
)oestra-4,15-dien-3-one
4'-[17β-hydroxy-17α-(1-propynyl)-3-oxo-oestra-4,15-
dien-11β-yl][1,1'-biphenyl]-4-carbonitrile
11β-[4-(3-furanyl)phenyl]-17β-hydroxy-17α-(1-
propynyl)oestra-4,15-dien-3-one
11β-(4-acetylphenyl)-17β-hydroxy-17α-(1-propynyl)o-
estra-4,15-dien-3-one
4'-[4',5'-dihydro-3-oxospiro[oestra-4,15-diene-
17β,2'(3'H)-furan]-11β-yl][1,1'-biphenyl]-4-carboni-
trile
(Z)-17β-hydroxy-17α-3-hydroxy-1-propenyl)-11β-(4-
methoxyphenyl)-oestra-4,15-dien-3-one
4'-[4',5'-dihydro-3-oxospiro[oestra-4,15-diene-
17β,2'(3'H)-furan]-11β-yl][1,1'-biphenyl]-4-carboni-
trile
11β-(4-acetylphenyl)-17α-ethynyl-17β-hydroxyoestra-
4,15-dien-3-one
4'-[17α-ethynyl-17β-hydroxy-3-oxo-oestra-4,15-dien-
11β-yl][1,1'-biphenyl]-4-carbonitrile
11β-[4-(dimethylamino)phenyl]-17β-hydroxy-17α-
methyloestra-4,15-dien-3-one The preparation of the compounds of the general formula I according to the invention is shown by the following reaction scheme:

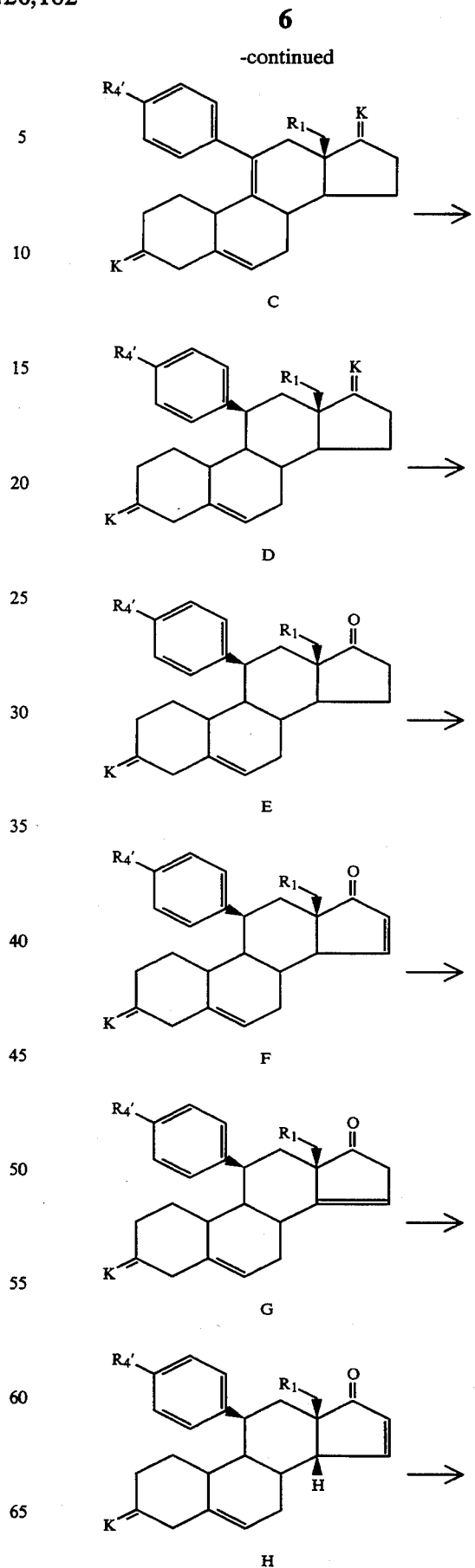

-continued

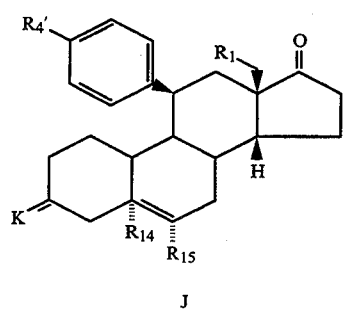

J

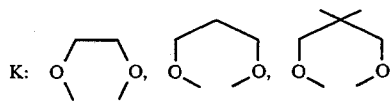

or other oxygen ketals

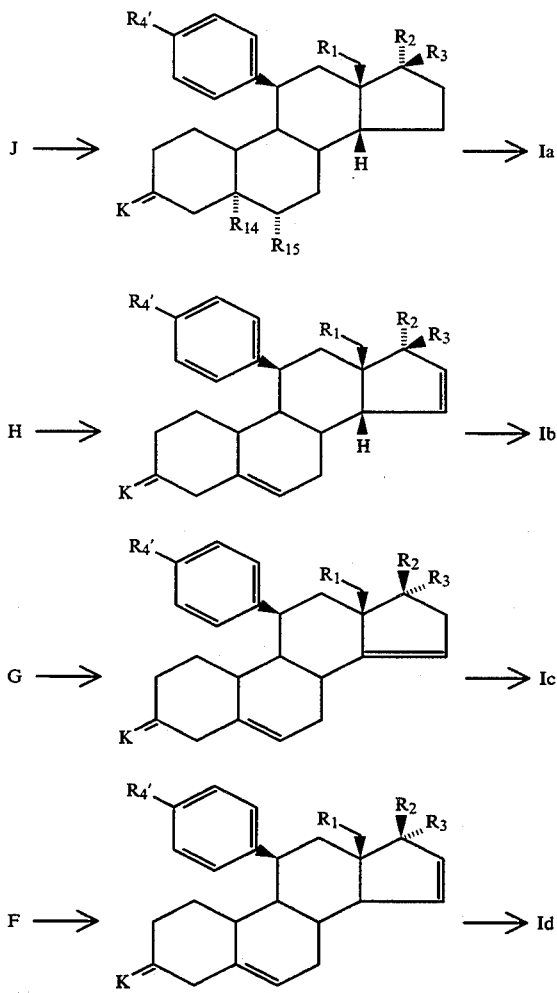

In accordance with the present invention, compound A (Recl. Trav. Chim. Bays-Pas 107, 331, (1988)) is first converted into a compound of formula B wherein L represents a perfluoroalkylsulphonyloxy group $C_nF_{2n+1}SO_2O$—(n=1,2,3 or 4).

Compound B is reacted, in the presence of a catalytic amount of a transition metal catalyst, with an aryl compound of the general formula Z

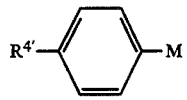 (Z)

in which M represents one of the radicals:

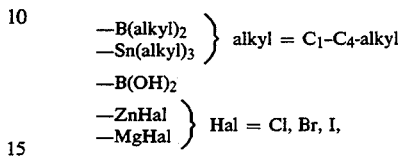

and $R^{4'}$ represents one of the radicals mentioned for $R^4$, to form a compound of the general formula C wherein $R^1$ has the meaning given in formula I and $R^{4'}$ has the meaning given in formula Z and optionally, if $R^4$ in formula I is to have a different meaning from $R^{4'}$ in formula C, a compound of the general formula C in which $R^{4'}$ represents a bromine atom or, after conversion of a methoxy group representing $R^{4'}$, a perfluoroalkylsulphonyloxy group $C_nF_{2n+1}SO_2O$— (n=1, 2, 3 or 4), is reacted with a compound of the general formula VI

$R^4$—M (VI)

in which $R^4$ has the meaning finally desired for that substituent in formula I and M has the meaning already given in formula Z.

L in compound B preferably represents the trifluoromethylsulphonyloxy group.

The transition metal catalyst used according to the Examples of the present invention for coupling the aryl compound of the general formula Z with the compound containing the leaving group L is palladium tetrakistriphenylphosphine (see literature indicated below); nickel tetrakistriphenylphosphine or similar transition metal catalysts could equally be used.

The variant that the ultimately desired substituent $R^4$ is introduced by the functionalisation of a bromine or methoxy substituent $R^{4'}$ in compound C is selected when the aryl compound of the general formula Z to be coupled, in which $R^{4'}$ is already identical to $R^4$, is not available or is not suitable for the coupling. Transition metal-catalysed aryl coupling reactions of compounds of the general formula Z-type with compounds carrying a leaving group are described, for example, in: —Sn(alkyl)3-substituted aromatic compounds: J. E. McMurry and S. Mohanraj, Tetrahedron Letters, 24, No. 27, pages 2723–2726, 1983; X. Lu and J. Zhu, Communications, pages 726–727, 1987; Q.-Y. Chen and Z.-Y. Yang, Tetrahedron Letters 27, No. 10, pages 1171–1174, 1986; S. Cacchi, P. G. Ciattini, E. Morera and G. Ortar, Tetrahedron Letters 27, No. 33, pages 3931–3934, 1986; A. M. Echavarren and J. K. Stille, J.Am. Chem. Soc. 1987, 109, pages 5478–5486 and J.Am. Chem. Soc. 1988, 110, page 1557; —B(OH)2— and —B(Oalkyl)2-substituted aromatic compounds: Y. Hoshino, N. Miyaura and A. Suzuki, Bull. Chem. Soc. Jpn. 61, 3008 (1988); H. Matsubasa, K. Seto, T. Tahara and S. Takahashi; Bull.- Chem. Soc. Jpn, 62, 3896 (1989); —ZnCl-substituted aromatic compounds: R. McCague, Tet. Lett., 28, 701 (1987); A. Arcadi, A. Burini, S. Cacchi, M. Delmastro, F. Marinelli, B. Pietroni, Syn. Les., 1, 1990, page 47.

The compounds of the general formula D, which are suitable as starting materials for the preparation of the 10β-H-steroids of the general formula I, can readily be prepared by reducing a compound of formula C, wherein $R^4$ and $R^1$ have the meanings given in the formulae, without destruction of the aromatic system and the 5,6-double bond, to a compound of the general formula D in which $R^4$ and $R^1$ have the meanings already given. On the reduction of C, the 11β-aryl compound D is formed (stereoselective reduction). Various methods are suitable in accordance with the invention for reducing the 9(11)-double bond in C: preferred in accordance with the invention is reduction with an electropositive metal in an electron-solvating solvent or in a solvent containing a solubiliser. There comes into consideration as electron-solvating solvent especially ammonia.

Equimolar amounts of reducing agent are sufficient for the reduction, but it is also possible for a substantial excess of reducing agent to be used without the aromatic system and/or the 5,6-double bond being attacked. Any metal suitable for a Birch reduction may be used as the electropositive metal. Preferred in accordance with the invention are lithium, potassium, sodium and calcium, with lithium being especially preferred.

Selective cleavage of the keto-protecting group in the 17-position by means of a weak acid (acetic acid, oxalic acid) yields compound E.

The intermediates of formula F having an unsaturated D-ring are obtainable, for example, by modified Saegusa oxidation (Tetrahedron 42, (1986) 297; EP-A 0 299 913) of the corresponding enol compound of the 17-ketone.

Base treatment of type F compounds, for example with silica gel/triethylamine, yields compounds G having a $\Delta^{14}$-double bond (S. Scholz et al., Liebigs Ann. Chem. 1989, 151). The compounds can be converted into the corresponding 14β-H compounds of formula H, for example by way of the corresponding trimethylsilyl enol ethers by treatment with hydrogen fluoride/pyridine complex.

Compounds of the H-type can be reduced, either by Birch reduction or with complex hydrides or trialkyltin hydrides catalysed by copper, to compounds of the general formula J, $R^{14}$ and $R^5$ in that case together forming a double bond.

Alternatively, compounds H can be epoxidised, for example with organic peracids or hydrogen peroxide in the presence of, for example, hexachloroacetone or nitrotrifluoroacetophenone. Subsequent reduction yields the compounds J in which $R^{14}$=OH and $R^{15}$=H. The last-mentioned variant has the advantage that hydrogenations to saturated 17-C side chains can be effected without selectivity problems.

Compounds of types H, J, G and F can be converted into compounds of the general formulae Ia-d. For that purpose, first of all the substituents $R^2$ and $R^3$ desired at the 17-C atom are introduced. This introduction is carried out analogously to processes known from the literature (e.g. J. Fried, J. A. Edwards, "Organic Reactions in Steroid Chemistry", Van Nostrand Reinhold Company, 1972, Vol. 1 and 2; "Terpenoids and Steroids", Specialist Periodical Report, The Chemical Society, London, Vol. 1-2) by nucleophilic addition to the C-17-ketone.

In the case of a readily enolisable 17-ketone, such as, for example, in the case of compound G, nucleophiles are introduced by adding cerium salts.

The stereochemical course of the addition of a nucleophile to the 17-keto group of compounds J, H, G and F depends on the siting of the hydrogen atom at the 14-C atom. If a 14β-configured H atom is present in J or H, the nucleophile enters in the β-configuration; if there is a double bond between C-14 and C-15 (G), or if there is an α-configured H atom at C-14 (F), entry is in the α-configuration.

The introduction of the substituent $-C\equiv C-Y$ as $R^3$, Y having the meaning given above, is carried out with the aid of a metallated compound of the general formula $MC\equiv C-Y'$ in which Y' is an alkyne-protecting group, such as, for example, trimethylsilyl or tert.-butyldimethylsilyl.

The organometallic compound can also be formed in situ and caused to react with the 17-ketone. For example, acetylene and an alkali metal, especially potassium, sodium or lithium, can be allowed to act on the 17-ketone in a suitable solvent in the presence of an alcohol or in the presence of ammonia. The alkali metal may also be in the form of, for example, methyl- or butyl-lithium. Suitable solvents are especially dialkyl ethers, tetrahydrofuran, dioxan, benzene and toluene.

The introduction of 3-hydroxypropyne or 3-hydroxypropene in the 17-position is effected by reacting the 17-ketone with the dianion of propargyl alcohol (3-hydroxypropyne), for example the propargyl alcohol dipotassium salt produced in situ, to form the 17α-(3-hydroxyprop-1-ynyl)-17β-hydroxy derivative, or with metallated derivatives of 3-hydroxypropyne, for example 1-lithium-3-(tetrahydropyran-2'-yloxy)-prop-1-yn-1-ide, to form the 17-[3-(tetrahydropyran-2'-yloxy)-prop-1-ynyl]-17β-hydroxy derivative, which can then be hydrogenated to the 17-(3-hydroxypropyl or hydroxypropenyl)-17β-hydroxy compounds. This is effected, for example, by hydrogenation at room temperature and normal pressure in solvents such as methanol, ethanol, propanol, tetrahydrofuran (THF) or ethyl acetate with the addition of noble metal catalysts, such as platinum or palladium.

Homologous hydroxyalkyne, hydroxyalkene and hydroxyalkane groups are introduced in a corresponding manner with homologues of propargyl alcohol.

The compound with the α-configured double bond in the hydroxypropenyl group is produced by hydrogenating the acetylenic triple bond with a deactivated noble metal catalyst (J. Fried, J. A. Edwards: Organic Reactions in Steroid Chemistry, Van Nostrand Reinhold Company 1972, page 134; and H. O. House: Modern Synthetic Reactions 1972, page 19). There come into consideration as deactivated noble metal catalysts, for example, 10% palladium-on-barium sulphate in the presence of an amine or 5% palladium-on-calcium carbonate with the addition of lead(II) acetate. The hydrogenation is discontinued after one equivalent of hydrogen has been taken up.

The compound with the E-configured double bond in the hydroxypropenyl group is produced by reducing the acetylenic triple bond in a manner known per se. Numerous methods of converting alkynes into trans-olefins are described in the literature, for example reduction with sodium in liquid ammonia (J. Am. Chem. Soc. 63 (1941) 216), with sodium amide in liquid ammonia (J. Chem. Soc. 1955, 3558), with lithium in low-molecular amines (J. A. Chem. Soc. 77 (1955) 3378), with boranes (J. Am. Chem. Soc. 93 (1971) 3395 and 94 (1972) 6560), with diisobutylaluminium hydride and methyllithium (J. Am. Chem. Soc. 89 (1967) 5085) and especially with lithium aluminium hydride/alcoholate (j. Am. Chem. Soc. 89 (1967) 4245). A further possibility is reduction of the triple bond with chromium(II) sulphate in the presence of water or dimethylformamide in weakly acidic medium (J. Am. Chem. Soc. 86 (1964) 4358) and, generally, reduction by the action of transition metal compounds alternating with an oxidation step.

The introduction of hydroxyalkenes can also be carried out directly, by adding a corresponding metallated hydroxyalkenyl compound, such as, for example, 1-lithium-3-(tetrahydropyran-2'-yloxy)-prop-1(E)-ene (J. Org. Chem. 40 2265) or 1-lithium-3-(tetrahydropyran-2'-yloxy)-prop-1(Z)-ene (Synthesis 1981, 999). Homologues can also be introduced in that manner.

The introduction of 3-hydroxypropane in the 17-position can also be carried out directly, by reacting the 17-ketone with metallated derivatives of 3-halopropanols—the hydroxy group in the metallisation step being in the form of an alcoholate (Tetrahedron Letters 1978, 3013) or in the form of a protected function (J. Org. Chem. 37, 1947)—to form the 17-(3-hydroxypropyl)-17$\beta$-hydroxy compound or the compound protected at the terminal hydroxy group, respectively. There come into consideration as protecting groups, for example, ethoxyethyl, tetrahydropyranyl and methoxymethyl groups. Alternatively, a 2-propenyl group may be added, which is then converted to the 3-hydroxypropane group by hydroborination, preferably with sterically hindered boranes, such as, for example, 9-borabicyclononane (9-BBN).

If end products of formula I are desired in which $R^2/R^3$ represent

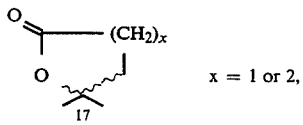

the 17-(3-hydroxypropyl) or 17-(4-hydroxybutyl) compound is oxidised in a manner known per se, for example with Jones' reagent, pyrolusite, pyridinium dichromate, pyridinium chlorochromate, chromic acid/pyridine or the fetizone reagent silver carbonate/Celite (Compt. rend. 267 [1968] 900).

The preparation of end products of formula I in which $R^2/R^3$ represent

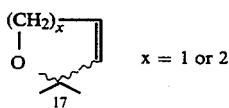

is carried out by a ring closure reaction of the corresponding 17-(3-hydroxyprop-1-(Z)-enyl- or 17-(4-hydroxybut-1-(Z)-enyl-17-$\beta$-hydroxy educt. Hydrogenation of the unsaturated 5- or 6-ring-spiro ether with palladium/activated carbon contact results in the saturated spiro ethers.

The introduction of the 17-cyanomethyl side chain is effected in a manner known per se from the 17-ketone, for example by way of the 17-spiro epoxide and cleavage of the spiro epoxide with HCN according to Z. Chem. 18, (1978) 259–260.

The introduction of the 17-hydroxyacetyl side chain is also carried out according to methods known per se, for example according to the methods described in J. Org. Chem. 47 (1982), 2993–2995, Chem. Ber. 113 (1984), 1184 and U.S. Pat. No. 4,600,538. Free hydroxy groups may be alkylated or acylated in a manner known per se.

The next reaction step serves to introduce the substituent $R^4$ or $R^{4'}$ in the p-position on the 11$\beta$-phenyl ring. This procedure is necessary when $R^4$ is not introduced directly during coupling of the compound B with the aryl compound Z to form compound C.

There is used as starting material for this introduction compound J, H, G or F wherein $R^4$=OH, which is obtainable from the corresponding methoxy compound by ether cleavage, for example with sodium ethanethiolate in a solvent, such as dimethylformamide.

By reacting the hydroxy compound with a perfluoro-($C_1$–$C_4$)-alkylsulphonic acid anhydride or halide in the presence of a base, such as pyridine or 4-(dimethylamino)-pyridine, the corresponding 11$\beta$-[4-(perfluoroalkylsulphonyloxy)phenyl] compound is obtained (P. J. Stang, M. Hanack and L. R. Subramanian, Synthesis 85, (1982)). In the subsequent coupling of the 11$\beta$-aryl compound with $R^{4''}$—Sn(Alkyl)3 or $R^{4''}$—BL$_2$, the procedure is either that in a transition metal-catalysed reaction (preferably Pd−) the perfluoroalkyl sulphonate leaving group is displaced with essentially almost simultaneous substitution by the desired substituent or a precursor thereof (Aryl couplings with tin compounds: J. E. McMurry and S. Mohanraj, Tetrahedron Letters, 34, No. 27, pages 2723–2726, 1983; X. Lu and J. Zhu, Communications, pages 726–727, 1987; Q.-Y. Chen and Z.-Y. Yang, Tetrahedron Letters, 27, No. 10, pages 1171–1174, 1986; S. Cacchi, P. G. Ciattini, E. Morera and G. Ortar, Tetrahedron Letters 27, No. 33, pages 3931–3934, 1986; A. M. Echavarren and J. K. Stille, J. Am. Chem. Soc. 1987, 109, pages 5478–5486; with boron compounds: Synthesis 936 (1984), Chem. Pharm. Bull. 33, 4755–4763 (1985); J.Org. Chem. 49, 5237–5243 (1984); Bull.Chem. Soc. Jpn. 61, 3008–3010$\beta$(1988)), or that there is produced as intermediate from the perfluoroalkyl sulphonate compound with transition metal-catalysis a corresponding tri-organylstannyl, preferably tri-n-alkylstannyl, compound [J. K. Stille, Angew. Chem. 98 (1986), pages 504–519]. This is then reacted in a one-pot reaction with a halogen-substituted, preferably a bromine- or iodine-substituted, carbocyclic or heterocyclic aromatic compound [Y. Yamamoto, Y. Azuma, H. Mitoh, Communications, pages 564–565, 1986; T. J. Bailey, Tetrahedron Letters, 27, No. 37, pages 4407–4410, 1986], which, if desired, may in addition carry further substituents; the 11$\beta$-phenyl radical then has the desired substitution or a precursor to the desired substitution. Numerous such reactions with steroids in which a trifluoromethanesulphonate group is located in the 4-position of an 11$\beta$-phenyl ring are described in EP-A-0283428. Free hydroxy groups may be alkylated or acylated in a manner known per se. Dialkylamines may be converted by suitable oxidising agents [for example hydrogen peroxide or peracids) into the desired N-oxides [see, for example, Kontakte (parmstadt) 1986, 3, page 12].

Compounds having a dialkylamine substituent on the 11$\beta$-phenyl ring may be converted into the corresponding (N-cyano-N-alkylaminoaryl) derivatives in good yield by reaction with cyanogen bromide in aprotic solvents, such as, for example, dioxan, benzene or toluene, at elevated temperature (amine degradation according to Braun) analogously to the directions given, for example, in Org. Reactions Z, 198 (1953), K. W. Bentley, Techniques of Organic Chemistry 11, 773 (1963) and Houben-Weyl, 5/4, 151 (1960).

Depending upon the desired final meaning of

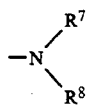

in the end product, the above derivatives are reduced in a manner known per se to the corresponding dialkylamine compounds (for example with diisobutylaluminium hydride in toluene to the N-formyl-N-alkylaminophenyl intermediates and then with lithium aluminium hydride) or N—H—N-alkyl compounds (for example with lithium aluminium hydride or with lithium in liquid ammonia). The latter are then, if desired, acylated in a manner known from the literature and optionally reduced in known manner with, for example, lithium aluminium hydride, to form the new dialkylamine derivative (see DE 36 23 038). If desired, it is also possible to introduce the substituent $R^4$ first and then introduce the substituents $R^2$ and $R^3$, depending upon whether the process conditions of the second reaction step adversely affect the substituents first introduced or built on.

Any protecting groups still present are removed according to current methods.

The resulting compounds of the general formula I in which X represents an oxygen atom can, if desired, be converted into the oximes (formula I in which X represents the hydroxyimino grouping $>N\sim OH$, wherein the hydroxy group may be in the syn- or anti-configuration) by reaction with hydroxylamine hydrochloride in the presence of tertiary amines at temperatures of from $-20°$ to $+40°$ C. Suitable tertiary bases are, for example, trimethylamine, triethylamine, pyridine, N,N-dimethylaminopyridine, 1,5-diazabicyclo[4.3.0]non-5-ene (DBN) and 1,8-diazabicyclo[5.4.0]undec-7-ene (DBU), with pyridine being preferred.

The removal of the 3-oxo group to form an end product of the general formula I in which X represents 2 hydrogen atoms can be carried out, for example, according to the directions given in DE-A-2805490 by reductive cleavage of the thioketal.

The novel compounds of the general formula I and the pharmacologically tolerable addition salts thereof with acids are valuable pharmaceutical agents. They exhibit a strong affinity for the gestagen receptor and surprisingly have pronounced antigestagenic and antiglucocorticoid, antimineralocorticoid and antiandrogenic properties. These important biological activities can be used for medicinal purposes.

The strong affinity to the gestagen receptor is demonstrated by the known gestagen receptor-binding test described inter alia in EP-A-0 190 759. The following compounds were examined:

17β-hydroxy-11β-(4-methoxyphenyl)-17α-methyloestra-5,14-dien-3-one (A)

11β-[4-(3-furanyl)phenyl]-17β-hydroxy-17α-methyloestra-4,14-dien-3-one (B)

11β-(4-acetylphenyl)-17β-hydroxy-17α-methyloestra-4,14-dien-3-one (C)

17β-hydroxy-17α-methyl-11β-[4-(3-thienyl)phenyl]oestra-4,14-dien-3-one (D)

11β-(4-acetylphenyl)-17β-hydroxy-17α-methyloestra-4,15-dien-3-one (E)

11β-[(3-furanyl)phenyl]-17β-hydroxy-17α-methyloestra-4,15-dien-3-one (F)

17β-hydroxy-11β-(4-methoxyphenyl)-17α-methyloestra-4,15-dien-3-one (G)

17β-hydroxy-17α-methyl-11β-[4-(3-pyridyl)phenyl]oestra-4,15-dien-3-one (H)

4'-[17β-hydroxy-17α-methyl-3-oxo-oestra-4,15-dien-11β-yl][1,1'-biphenyl]-4-carbonitrile (I)

The compounds examined have the following competition factors (reference substance: $^3$H-progesterone; rabbit uterus tissue)

| Test compound | A | B | C | D | E | F | G | H | I |
|---|---|---|---|---|---|---|---|---|---|
| Competition factor K | 2.5 | 2.6 | 4.0 | 3 | 2.6 | 1 | 3.2 | 0.6 | 0.7 |

In order to characterise the antigestagenic activity, the abortive action on gravid rats was determined according to the test described in EP-A 0 283 428.

Compounds B, C, E and F were examined (see Table 1).

Administration of the test compounds on d5-d7 p.c.p.o.; autopsy on d9 p.c.

Active substances of this kind having pronounced antigestagenic activity are suitable for inducing abortion since they displace from the receptor the progesterone necessary for maintaining the pregnancy. They are therefore valuable and of interest in view of their use for post-coital fertility control.

The novel compounds can furthermore be used for treating endometriosis. They can also be employed to treat hormone irregularities, trigger menstruation and induce birth. In addition they can be used for the treatment of hormone-dependent carcinomas.

The compounds of the general formula I and their pharmacologically tolerable addition salts with acids also exhibit an antiglucocorticoid activity and can therefore also be used as medicaments for the treatment of corticoid-induced disorders (glaucoma) and to control side-effects that arise in the case of long-term treatment with glucocorticoids (Cushing's syndrome). They therefore also make it possible to control disorders attributable to a supersecretion of glucocorticoids, especially adiposity, arteriosclerosis, hypertension, osteoporosis, diabetes and insomnia.

The compounds of the general formula I according to the invention and their pharmacologically tolerable addition salts with acids having antiandrogenic activity can be used in the treatment of hypertrophy and carcinomas of the prostate. They also render possible a specific treatment of androgenisation phenomena in women: pathological hairiness in hirsutism, androgenetic alopecia, and the increased sebaceous gland function in acne and seborrhoea can be favourably influenced.

The invention thus also relates to medicaments based on compounds of the general formula I and the pharmacologically tolerable addition salts thereof with acids, optionally together with customary excipients and carriers.

The compounds according to the invention and salts thereof can be processed according to methods of galenical pharmacy that are known per se into pharmaceutical compositions for enteral, percutaneous, parenteral or local administration. They can be administered in the form of tablets, dragees, gelatin capsules, granules, suppositories, implants, injectable sterile aqueous or oily solutions, suspensions or emulsions, ointments, creams and gels. The active ingredient or ingredients may be mixed with excipients customary in galenical pharmacy, such as, for example, gum arabic, talc, starch, mannitol, methylcellulose, lactose, surfactants such as Tweens ® or Myrj ®, magnesium stearate, aqueous or non-aqueous carriers, paraffin derivatives, wetting agents, dispersing agents, emulsifying agents, preservatives and flavourings for taste correction (for example ethereal oils). The invention therefore also relates to pharmaceutical compositions that comprise as active ingredient at least one compound according to the invention or a pharmacologically tolerable addition salt thereof with acids. There may be mentioned as addition salts of the products according to the invention with acids especially the hydrochlorides and the methanesulphonates. One unit dose contains approximately 1–100 mg of active ingredient(s). The dose of the compounds according to the invention for humans is approximately 1–1000 mg per day.

The following Examples serve to illustrate the invention in more detail:

EXAMPLE 1

11β-(4-Acetylphenyl)-17α-hydroxy-17β-(3-hydroxypropyl)-14β-oestr-4-en-3-one a)

3,3;17,17—Bis[1,2-ethanediylbis(oxy)]-11-[[(trifluoromethyl)sulphonyl]oxy]oestra-5,9(11)-diene 26.1 g of 3,3;17,17-bis[1,2-ethanediylbis(oxy)]estr-5-en-11-one are dissolved in 350 ml of absolute methylene chloride, and 18 ml of 2,6-di-tert.-butylpyridine are added under inert gas. After cooling this solution to 0° C., 12.9 ml of trifluoromethanesulphonic acid anhydride are slowly added dropwise. The reaction mixture is subsequently stirred for 20 hours at room temperature. For working up, the reaction mixture is poured onto saturated sodium hydrogen carbonate solution, the organic phase is removed and the aqueous phase is then extracted with methylene chloride. The combined organic phases are washed with saturated sodium chloride solution, dried over sodium sulphate and concentrated in vacuo. Chromatography of the crude product on silica gel with a mixture of ethyl acetate/hexane yields, in addition to 16.4 ml of 2,6-di-tert.-butylpyridine and 5.1 g of 3,3;17,17-bis[1,2-ethanediylbis(oxy)]oestr-5-en-11-one, 27 g of 3,3;17,17-bis[1,2-ethanediylbis(oxy)]-11-[[(trifluoromethyl)sulphonyl]oxy]oestra-5,9(11)-diene in the form of a white foam.

$[\alpha]_D^{20} = +104°$ (CHCl$_3$; C=0.505)

$^1$H-NMR (CDCl$_3$) ε: 5.58 dbr (J=5 Hz, 1H, H-6); 3.7–4.0 m (8H, m, ketals); 2.88 dbr (J=11 Hz, 1H, H-10); 2.74 dtr (J=16, 2.5 Hz, 1H, H-12); 2.18–2.33 m (2H, H-4); 0.84 s (3H, H-18).

b)

3,3;17,17—Bis[1,2-ethanediylbis(oxy)]-11-(4-methoxyphenyl)oestra-5,9(11)-diene 27 g of 3,3;17,17-bis[1,2-ethanediylbis(oxy)]-11-[[(trifluoromethyl)sulphonyl]oxy]oestra-5,9(11)-diene are dissolved in a mixture of 450 ml of absolute toluene and 210 ml of absolute ethanol, and 3.1 g of palladium tetrakistriphenylphosphine, 4.5 g of lithium chloride, 70 ml of 2 molar sodium carbonate solution and 9 g of 4-methoxyphenylboronic acid are added in succession. The reaction mixture is then stirred for 2 hours at 95° C. and cooled to room temperature, and saturated sodium chloride solution is added. The organic phase is removed, washed in succession with 5% sodium hydroxide solution and water, dried over sodium sulphate and concentrated in vacuo. The residue is chromatographed on silica gel with a mixture of ethyl acetate/hexane. 24 g of 3,3;17,17bis[1,2-ethanediylbis(oxy)]-11-(4-methoxyphenyl)oestra-5,9(11)-diene are obtained in the form of a white foam.

c)

3,3;17,17—Bis[1,2-ethanediylbis(oxy)]-11β-(4-methoxyphenyl)oestr-5-ene 1000 ml of ammonia are condensed at −70° C. and 1.80 g of lithium is added. After the characteristic blue colouring appears, 24 g of 3,3;17,17-bis[1,2-ethanediylbis(oxy)]-11β-(4-methoxyphenyl)oestra-5,9(11)-diene dissolved in 500 ml of absolute tetrahydrofuran are added dropwise. After stirring the mixture for 20 minutes, the excess lithium is decomposed by the addition of water and the ammonia is evaporated off. The reaction mixture is poured onto saturated ammonium chloride solution and the aqueous phase is extracted with ethyl acetate. The combined organic phases are washed with saturated sodium chloride solution, dried over sodium sulphate and concentrated in vacuo. After chromatography of the crude product on silica gel with a mixture of ethyl acetate/hexane, 19.6 g of 3,3;17,17-bis[1,2-ethanediylbis(oxy)]-11β-(4-methoxyphenyl)oestr-5-ene and 1.8 g of 3,3;17,17bis[1,2-ethanediylbis(oxy)]-11-(4-hydroxyphenyl)oestra-5,9(11)-diene are isolated in the form of white foams.

d)

3,3-[1,2-Ethanediylbis(oxy)]-11β-(4-methoxyphenyl)oestr-5-en-17-one 60 g of silica gel are suspended in 130 ml of methylene chloride, 5.9 ml of saturated oxalic acid solution are added and the mixture is then stirred for 15 minutes. There are added to this suspension 19.6 g of 3,3;17,17bis[1,2-ethanediylbis(oxy)]-11β-(4-methoxyphenyl)oestr-5-ene, and the reaction mixture is then stirred at room temperature for 4 hours and subsequently filtered off with suction through a frit. The frit residue is then washed with methanol/methylene chloride and the filtrate so obtained is extracted by shaking with saturated sodium hydrogen carbonate solution. The organic phase is dried over sodium sulphate and concentrated in vacuo. The residue is chromatographed on silica gel with a mixture of ethyl acetate/hexane. 13.77 g of 3,3-[1,2-ethanediylbis(oxy)]-11β-(4-methoxyphenyl)oestr-5-en-17-one are obtained in the form of a white foam.

e)

3,3-[1,2-Ethanediylbis(oxy)]-11β-(4-methoxyphenyl)-17-[(trimethylsilyl)oxy]oestra-5,16-diene Lithium diisopropylamide is produced at −30° C. from 14.07 ml of diisopropylamine and 72 ml of a 1.6 molar solution of n-butyllithium in hexane. 3,3-[1,2-Ethanediylbis(oxy)]-11β-(4-methoxyphenyl)oestr-5-en-17-one (28.28 g dissolved in 250 ml of absolute tetrahydrofuran) is added dropwise thereto. The whole is then stirred at 0° C. for 15 minutes. 24.3 ml of trimethylchlorosilane are then added dropwise. The whole is stirred at 0° C. for a further 15 minutes and the reaction solution is poured onto saturated sodium hydrogen carbonate solution and extracted with ethyl acetate. The organic phase is washed with saturated ammonium chloride solution and with saturated sodium chloride solution, dried over sodium sulphate and concentrated in vacuo. The crude product is recrystallised from acetonitrile. 25.65 g of 3,3-[1,2-ethanediylbis(oxy)]-11β-(4-methoxyphenyl)-17-[(trimethylsilyl)oxy]oestra-5,16-diene are obtained.

f)
3,3-[1,2-Ethanediylbis(oxy)]-11β-(4-methoxyphenyl)oestra-5,15-dien-17-one 25.65 g of 3,3-[1,2-ethanediylbis(oxy)]-11β-(4-methoxyphenyl)-17-[(trimethylsilyl)oxy]oestra-5,16-diene are dissolved in 390 ml of acetonitrile. Under argon, 17.36 g of palladium(II) acetate are added and the whole is stirred overnight at room temperature. The reaction solution is then filtered through Celite and concentrated. The crude product is purified by column chromatography on silica gel with hexane/ethyl acetate. 16.6 g of 3,3-[1,2-ethanediylbis(oxy)]-11β-(4-methoxyphenyl)oestra-5,15-dien-17-one are obtained.

$^1$H-NMR (CDCl$_3$): δ=7.53 dd (J=6, 1 Hz, 1H, H-15); 7.25 d (J=10 Hz, 2H, Ar); 6.80 d (J=10 Hz, 2H, Ar); 5.98 dd (J=6, 3 Hz, 1H, H-16); 5.57 dbr (J=5 Hz, 1H, H-6 ); 3.87–4.00 (4H, ketal); 3.79 s (3H, OMe); 3.51 ddbr (J=5, 6 Hz, 1H, H-11); 0.90 s (3H, H-18)

g)
3,3-[1,2-Ethanediylbis(oxy)]-11β-(4-methoxyphenyl)oestra-5,14-dien-17-one 16.6 g (39.47 mmol) of 3,3-[1,2-ethanediylbis(oxy)]-11β-(4-methoxyphenyl)oestra-5,15-dien-17-one are dissolved in 3 l of ethyl acetate/hexane (9:1). Under argon, 1.3 kg of silica gel and 240 ml of triethylamine are added. The mixture is then stirred at room temperature for 60 hours. The reaction solution is subsequently filtered and concentrated in vacuo. The crude product is purified by column chromatography (hexane/ethyl acetate +1% triethylamine). 10.04 g of 3,3-[1,2-ethanediylbis(oxy)]-11β-(4-methoxyphenyl)oestra-5,14-dien-17-one are obtained in the form of a white foam.

$^1$H-NMR (CDCl$_3$): δ=7.33 d (J=10 Hz, 2H, Ar); 6.83 d (J=10 Hz, 2H, Ar); 5.60 m (2H, H-6, H-15); 3.90–4.01 m (4H, ketal); 3.80 s (3H, OMe); 3.39 ddbr (J=7, 5 Hz, 1H, H-11); 0.80 s (3H, H-18)

h)
3,3-[1,2-Ethanediylbis(oxy)]-11β-(4-methoxyphenyl)-14β-oestra-5,15-dien-17-one Lithium diisopropylamide is produced at −30° C. from 5.03 ml of diisopropylamine and 25.34 ml of n-butyllithium (1.6 molar solution in hexane). A solution of 10 g of 3,3-[1,2-ethanediylbis(oxy)]-11β-(4-methoxyphenyl)oestra-5,14-dien-17-one in 200 ml of absolute tetrahydrofuran is added dropwise thereto. The mixture is stirred at 0° C. for 15 minutes and then 8.61 ml of trimethylchlorosilane are added dropwise. The mixture is stirred at 0° C. for a further 15 minutes. The reaction solution is then cooled to −78° C. and 6 ml of hydrogen fluoride/pyridine complex are added dropwise thereto. The mixture is then stirred at −40° C. for 2 hours. The reaction solution is subsequently poured onto saturated sodium hydrogen carbonate solution and extracted with ethyl acetate. The organic phase is washed with saturated sodium chloride solution, dried over sodium sulphate and concentrated in vacuo. The crude product is recrystallised from diisopropyl ether. 7.4 g of 3,3-[1,2-ethanediylbis(oxy)] -11β-(4-methoxyphenyl)-14β-oestra-5,15-dien-17-one are obtained in the form of white crystals.

$^1$H-NMR (CDCl$_3$): δ=7.78 dd (J=6, 2 Hz, 1H, H-15); 7.02 d (J=9 Hz, 2H, Ar); 6.77 d (J=9 Hz, 2H, Ar); 6.36 dd (J=6, 1.5 Hz, 1H, H-16); 5.50 m (1H, H-6); 3.78–3.95 m (4H, ketal); 3.76 s (3H, OMe); 2.73 ddd (J=11.5, 10.5, 6 Hz, 1H, H-11); 2.62 m (1H, H-14); 1.10 s (3H, H-18)

i)
3,3-[1,2-Ethanediylbis(oxy)]-11β-(4-methoxyphenyl)-5,6α-epoxy-5α,14β-oestr-15-en-17-one 7.40 g of 3,3-[1,2-ethanediylbis(oxy)]-11β-(4-methoxyphenyl)-14β-oestra-5,15-dien-17-one are dissolved in 200 ml of absolute methylene chloride. The mixture is cooled to 0° C. and 5.3 ml of saturated sodium hydrogen carbonate solution and 1.69 g of m-nitrotrifluoroacetophenone are added. 7 ml of a 30% H$_2$O$_2$ solution are then slowly added dropwise. The whole is stirred at room temperature for 7 days. Then saturated sodium thiosulphate solution is cautiously added to the reaction solution with gentle cooling. The whole is stirred for a further 30 minutes at room temperature and extracted with methylene chloride. The organic phase is washed twice with 5% sodium hydroxide solution and once with saturated sodium chloride solution and dried over sodium sulphate. The crude product is purified by column chromatography on silica gel with a mixture of hexane and ethyl acetate. 2.55 g of starting materials and 4.16 g of 3,3-[1,2-ethanediylbis(oxy)]-11β-(4-methoxyphenyl)-5,6α-epoxy-5α,14β-oestr-15-en-17-one are obtained.

$^1$H-NMR (CDCl$_3$): δ=7.72 dd (J=6, 2 Hz, 1H, H-15); 7.06 d (J=9 Hz, 2H, Ar); 6.78 d (J=9 Hz, 2H, Ar); 6.38 dd (J=6, 1.5 Hz, 1H, H-16); 3.82–3.97 m (4H, ketal); 3.78 s (3H, OMe); 2.94 dbr (J=4.5, 1H, H-6); 2.76 ddd (J=12.5, 9.5, 6 Hz, 1H, H-11); 2.68 m (1H, H-14); 1.04 s (3H, H-18)

k)
3,3-[1,2-Ethanediylbis(oxy)]-11β-(4-methoxyphenyl)-5α,14β-oestrane-5,17α-diol 4.16 g of 3,3-[1,2-ethanediylbis(oxy)]-11β-(4-methoxyphenyl)-5,6α-epoxy-5α,14β-oestr-15-en-17-one are dissolved in 200 ml of absolute ethanol. 5.54 g of sodium borohydride are cautiously added and the mixture is boiled under reflux for 1 hour. The reaction solution is then poured into water and extracted with methylene chloride. The organic phase is washed with saturated sodium chloride solution, dried over sodium sulphate and concentrated in vacuo. 3.98 g of 3,3-[1,2-ethanediylbis(oxy)]-11β-(4-methoxyphenyl)-5e,14β-oestrane-5,17α-diol are obtained. The crude product is used in the next step without being purified.

$^1$H-NMR (CDCl$_3$): δ=7.33 d (J=9, 2H, Ar); 6.28 d (J=9, 2H, Ar); 3.85–3.98 m (4H, ketal); 3.80 s (3H, OMe); 3.58 dd (J=9, 7.5 Hz, 1H, H-17); 3.12 ddbr (J=7, 6 Hz, 1H, H-11); 0.72 s (3H, H-18)

l)
3,3-[1,2-Ethanediylbis(oxy)]-11β-(4-methoxyphenyl)-5-hydroxy-5e,14β-oestran-17-one 5.50 g of chromium trioxide are added at 0° C. to a mixture of 35.6 ml of pyridine and 250 ml of methylene chloride. The whole is stirred for 30 minutes and then a solution of 3.98 g of 3,3-[1,2-ethanediylbis(oxy)]-11β-(4-methoxyphenyl)-5α,14β-oestrane-5,17α-diol in 70 ml of methylene chloride is added dropwise thereto. The whole is then stirred for 1.5 hours at approximately 10° C.— The reaction solution is washed twice with 5% sodium hydroxide solution and once with saturated sodium chloride solution, dried over sodium sulphate and concentrated in vacuo. The crude product is purified by column chromatography on silica gel with a mixture of hexane/ethyl acetate. 3.53 g of 3,3-[1,2-ethanediylbis(oxy)]-11β-(4-methoxyphenyl)-5-hydroxy-5α,14β-oestran-17-one are obtained.

$^1$H-NMR (CDCl$_3$): δ=7.31 d (J=10, 2H, Ar); 6.78 d (J=10, 2H, Ar); 3.85–4.00 m (4H, ketal); 3.80 s (3H, OMe); 3.10 ddbr (J=7, 6 Hz, 1H, H-11); 0.76 s (3H, H-18)

m)
3,3-[1,2-ethanediylbis(oxy)]-11β-(4-methoxyphenyl)-17β-[3-[(tetrahydro-2H-pyran-2-yl)oxy]-1-propynyl]-5α,14β-oestrane-5,17α-diol The organolithium compound is prepared at 0° C. from 11.23 g of 3-[(tetrahydro-2H-pyran-2-yl)oxy]-1-propyne in 350 ml of absolute tetrahydrofuran and 50.7 ml of a 1.6 molar solution of butyllithium in hexane. A solution of 3.53 g of 3,3-[1,2-ethanediylbis(oxy)]-11β-(4-methoxyphenyl)-5-hydroxy-5α,14β-oestran-17-one in 70 ml of absolute tetrahydrofuran is then added dropwise thereto and the whole is subsequently stirred at 0° C. for 1 hour. Saturated ammonium chloride solution is added and the mixture is extracted with ethyl acetate. The organic phase is washed with saturated sodium chloride solution, dried over sodium sulphate and concentrated in vacuo. The crude product is purified by column chromatography on silica gel with a mixture of hexane and ethyl acetate. 4.54 g of 3,3-[1,2-ethanediylbis(oxy)]-11β-(4-methoxyphenyl)-17β-[3-[(tetrahydro-2H-pyran-2-yl)oxy]-1-propynyl]-5e,14β-oestrane-5,17α-diol are obtained.

$^1$H-NMR (CDCl$_3$): δ=7.33 d (J=9 Hz, 2H, Ar); 6.79 d (J=9 Hz, 2H, Ar); 4.78 m (1H, THP); 4.28 sbr (2H, CH$_2$OTHP); 3.85–4.00 m (4H, ketal); 3.50 m (1H, THP); 3.15 m (1H, THP); 0.83 s (3H, H-18).

n)
3,3-[1,2-Ethanediylbis(oxy)]-11β-(4-methoxyphenyl)-17β-[3-[(tetrahydro-2H-pyran-2-yl)oxy]propyl]-5e,14β-oestrane-5,17α-diol 4.54 g of 3,3-[1,2-ethanediylbis(oxy)]-11β-(4-methoxyphenyl)-17β-[3-[(tetrahydro-2H-pyran-2-yl)oxy]-1-propynyl]-5α,14β-oestrane-5,17α-diol are dissolved in 300 ml of tetrahydrofuran/ethanol (1:1). 940 mg of palladium-on-calcium carbonate are added in argon countercurrent, and the apparatus is placed under hydrogen. The reactants are left to react for 3 hours at room temperature. The reaction solution is then filtered through Celite and concentrated. The crude product is purified by column chromatography on silica gel with a mixture of hexane/ethyl acetate. 4.29 g of 3,3-[1,2-ethanediylbis(oxy)]-11β-(4-methoxyphenyl)-17β-[3-[(tetrahydro-2H-pyran-2yl)oxy]propyl]-5α,14β-oestrane-5,17α-diol are obtained.

$^1$H-NMR (CDCl$_3$): δ=7.31 d (J=9 Hz, 2H, Ar); 6.78 d (J=9 Hz, 2H, Ar); 4.58 m (1H, THP); 3.70–3.95 (6H); 3.80 s (3H, OMe); 3.35–3.55 m (2H); 3.16 ddbr (J=7, 5 Hz, 1H, H-11); 0.65 s (3H, H-18); 0.63 s (3H, H-18) (isomeric THP ethers)

o)
3,3-[1,2-Ethanediylbis(oxy)]-11β-(4-hydroxyphenyl)-17β-[3-[(tetrahydro-2H-pyran-2-yl)oxy]propyl]-5α,14β-oestrane-5,17α-diol 4.29 g of 3,3-[1,2-ethanediylbis(oxy)]-11β-(4-methoxyphenyl)-17β-[3-[(tetrahydro-2H-pyran-2-yl)oxy]propyl]-5α,14β-oestrane-5,17α-diol are dissolved in 45 ml of absolute dimethylformamide. 2.05 g of sodium methanethiolate are added and the mixture is boiled under reflux for 1.5 hours. The reaction solution is then poured onto 100 ml of ice-cold aqueous sodium chloride solution and subsequently stirred overnight and suction-filtered. The filtrate is washed repeatedly with water, taken up in methylene chloride, washed with saturated sodium chloride solution, dried over sodium sulphate and concentrated in vacuo. The crude product is purified by column chromatography on silica gel with a mixture of hexane/ethyl acetate. 2.42 g of 3,3-[1,2-ethanediylbis(oxy)]-11β-(4-hydroxyphenyl)-17β-[3-[(tetrahydro-2H-pyran-2-yl)oxy]propyl]-5α,14β-oestrane-5,17α-diol are obtained.

$^1$H-NMR (CDCl$_3$): δ=7.25 d (J=9 Hz, 2H, Ar); 6.70 d (J=9 Hz, 2H, Ar); 4.59 m (1H, THP); 3.68–3.97 m (6H); 3.35–3.55 m (2H); 3.13 m (1H, H-11); 0.63 s (3H, H-18); 0.62 s (3H, H-18) (isomeric THP ethers)

p) 3,3-[1,2-Ethanediylbis(oxy)]-17β-[3-[(tetrahydro-2H-pyran-2-yl)oxy]propyl]-11β-[4-[[(trifluoromethyl)sulphonyl]oxy]phenyl]-5α,14β-oestrane-5,17α-diol 2.42 g of 3,3-[1,2-ethanediylbis(oxy)]-11β-(4-hydroxyphenyl)-17β-[3-[(tetrahydro-2H-pyran-2-yl)oxy]propyl]-5α,14β-oestrane-5,17α-diol are dissolved in 45 ml of absolute methylene chloride. 2.59 g of 4-dimethylaminopyridine are added and the whole is cooled to −78° C. 0.92 ml of trifluoromethanesulphonic acid anhydride are then slowly added dropwise. The whole is subsequently stirred at −78° C. for 6 hours. The reaction solution is then poured onto saturated sodium hydrogen carbonate solution and extracted with methylene chloride. The organic phase is washed with saturated sodium chloride solution, dried over sodium sulphate and concentrated in vacuo. The crude product is purified by column chromatography on silica gel with a mixture of hexane/ethyl acetate. 2.15 g of 3,3-[1,2-ethanediylbis(oxy)]-17β-[3-[(tetrahydro-2H-pyran-2-yl)oxy]propyl]-11β-[4-[[(trifluoromethyl)sulphonyl]oxy]phenyl]-5α,14β-oestrane-5,17α-diol are obtained.

$^1$H-NMR (CDCl$_3$): δ=7.49 d (J=9 Hz, 2H, Ar); 7.15 d (J=9 Hz, 2H, Ar); 4.58 m (1H, THP); 3.70–3.98 m (6H); 3.33–3.55 m (2H); 3.24 m (1H, H-11); 0.60 s (3H, H-18); 0.61 s (3H, H-18) (isomeric THP ethers)

q)
3,3-[1,2-Ethanediylbis(oxy)]-11β-[4-(1-ethoxyethenyl)phenyl]-17β-[3-[(tetrahydro-2H-pyran-2-yl)oxy]propyl]-5α,14β-oestrane-5,17α-diol 1.08 g of 3,3-[1,2-ethanediylbis(oxy)]-17β-[3-[(tetrahydro-2H-pyran-2-yl)oxy]propyl]-11β-[4-[[(trifluoromethyl)sulphonyl]oxy]phenyl]-5α,14β-oestrane-5,17α-diol are dissolved in 15 ml of dioxan. 0.67 ml (1.99 mmol) of (1-ethoxyvinyl)tributyltin, 91 mg (0.08 mmol) of tetrakis(triphenylphosphine)palladium, 130 mg (3.06 mmol) of lithium chloride and 0.161 ml (1.99 mmol) of pyridine are added thereto. The mixture is then boiled under reflux for 1 hour. The reaction solution is then filtered through Celite. The crude product obtained is purified by column chromatography on silica gel with a mixture of hexane/ethyl acetate. 583 mg of 3,3-[1,2-ethanediylbis(oxy)]-11β-[4-(1-ethoxyethenyl)phenyl]-17β-[3-[(tetrahydro-2H-pyran-2-yl)oxy]propyl]-5α,14β-oestrane-5,17α-diol and 143 mg of 11β-[4-acetylphenyl]-3,3-[1,2-ethanediylbis(oxy)]-17β-[3-[(tetrahydro-2H-pyran-2-yl)oxy]propyl]-5α,14β-oestrane-5,17α-diol are obtained.

r)

11β-(4-Acetylphenyl)-17α-hydroxy-17β-(3-hydroxypropyl)-14β-oestr-4-en-3-one 583 mg of 3,3-[1,2-ethanediylbis(oxy)]-11β-[4-(1-ethoxyethenyl)phenyl]-17β-[3-[(tetrahydro-2H-pyran-2-yl)oxy]propyl]-5α,14β-oestrane-5,17α-diol and 143 mg of 11β-[ 4-acetylphenyl]-3,3-[1,2-ethanediylbis(oxy)]-17β-[3-[(tetrahydro-2H-pyran-2-yl)oxy]propyl]-5α,14β-oestrane-5,17α-diol are dissolved in 25 ml of acetone. 1.15 ml of a 4 molar aqueous hydrochloric acid solution are added thereto and the whole is stirred at 50° C. for 1 hour. Saturated sodium hydrogen carbonate solution is then added and the mixture is extracted with methylene chloride. The organic phase is washed with saturated sodium chloride solution, dried over sodium sulphate and concentrated in vacuo. The crude product is purified by column chromatography on silica gel with a mixture of hexane/ethyl acetate. 420 mg of 11β-(4-acetylphenyl)-17α-hydroxy-17α-(3-hydroxypropyl)-14β-estr-4-en-3-one are obtained.

$^1$H-NMR (CDCl$_3$): δ=7.90 d (J=9 Hz, 2H, Ar); 7.54 d (J=9 Hz, 2H, Ar); 5.83 sbr (1H, H-4); 3.60–3.77 m (2H, CH$_2$OH); 3.45 ddbr (J=9, 5 Hz, 1H, H-11); 2.60 s (3H, OAc ); 0.72 s (3H, H-18)

EXAMPLE 2

17α-Hydroxy-17β-(3-hydroxypropyl)-11β-[4-(3-pyridinyl)phenyl]-14β-oestr-4-en-3-one a) 3,3–1,2-[Ethanediylbis(oxy)]-11β-[4-(3-pyridinyl)phenyl ]-17β-[3-[(tetrahydro-2H-pyran-2-yl)oxy]propyl]-5α,14β-oestrane-5,17α-diol 1.08 g of 3,3-[1,2-ethanediylbis(oxy)]-17β-[3-[(tetrahydro-2H-pyran-2-yl)oxy]propyl]-11β-[4-[[(trifluoromethyl)sulphonyl]oxy]phenyl]-5α,14β-oestrane-5,17α-diol are dissolved in 15 ml of toluene and 6.5 ml of ethanol. 250 mg of diethyl(3-pyridinyl)borane, 90 mg of tetrakis(triphenylphosphine)palladium, 132 mg of lithium chloride and 2 ml of a 2 molar sodium carbonate solution are added, and the mixture is boiled under reflux for 1 hour. The reaction mixture is subsequently diluted with water and then extracted with ethyl acetate. The organic phase is washed with saturated aqueous sodium chloride solution, dried over sodium sulphate, filtered and concentrated in vacuo. Column chromatography on silica gel with a mixture of hexane/ethyl acetate yields 774 mg of 3,3-1,2-[ethanediylbis(oxy)]-11β-[4-(3-pyridinyl)phenyl]-17β-[3-[(tetrahydro-2H-pyran-2-yl)oxy]propyl]-5α,14β-oestrane-5,17α-diol.

b)

17α-Hydroxy-17β-(3-hydroxypropyl)-11β-[4-(3-pyridinyl)phenyl]-14β-oestr-4-en-3-one 476 mg of 17α-hydroxy-17β-(3-hydroxypropyl)-11β-[4-(3-pyridinyl)-phenyl]-14β-oestr-4-en-3-one are prepared in the manner described in Example 1 r) from 774 mg of 3,3-[1,2-ethanediylbis(oxy)]-11β-[4-(3-pyridinyl)phenyl]-17β-[3-[(tetrahydro-2H-pyran-2-yl)oxy]propyl]-5α,14β-oestrane-5,17α-diol in 25 ml of acetone and 1.5 ml of 4 molar aqueous hydrochloric acid.

$^1$H-NMR (CDCl$_3$): δ=8.87 sbr (1H, Py); 8.58 dbr (J=4.5 Hz, 1H, Py); 7.87 dtr (J=7.5, 1Hz, 1H, Py); 7.53 m (4H, Ar); 7.37 dd (J=7.5, 4 Hz, 1H, Py); 5.83 sbr (1H, H-4); 3.60–3.78 m (2H, CH$_2$OH); 3.45 ddbr (7.5, 5, 1H, H-11); 0.77 s (3H, H-18)

EXAMPLE 3

17β-Hydroxy-11β-(4-methoxyphenyl)-17α-methyloestra-4,14-dien-3-one a)

3,3-[1,2-Ethanediylbis(oxy)]-11β-(4-methoxyphenyl)-17α-methyloestra-5,14-dien-17β-ol 2.46 g of anhydrous cerium trichloride are suspended in 20 ml of absolute tetrahydrofuran. The suspension is stirred at room temperature for 2 hours, and then cooled to 0° C., and 3.3 ml of a 3 molar solution of methylmagnesium chloride in tetrahydrofuran are added. The whole is subsequently stirred at 0° C. for one and a half hours and then a solution of 1 g of 3,3-[1,2-ethanediylbis(oxy)]-11β-[4-methoxyphenyl)oestra-5,14-dien-17-one in 10 ml of absolute tetrahydrofuran is added dropwise thereto. The whole is stirred at 0° C. for a further 1½ hours. The reaction solution is then poured onto saturated ammonium chloride solution and extracted with ethyl acetate, and the organic phase is washed with saturated sodium chloride solution and dried over sodium sulphate. The crude product is purified by column chromatography on silica gel with a mixture of hexane and ethyl acetate. 920 mg of 3,3-[1,2-ethanediylbis(oxy)]-11β-(4-methoxyphenyl)-17α-methyloestra-5,14-dien-17β-ol are obtained in the form of a white foam.

$^1$H-NMR (CDCl$_3$): δ=7.33 d (J=9 Hz, 2H, Ar); 6.81 d (J=9 Hz, 2H, Ar); 5.59 m (1H, H-15); 3.88–4.00 m (4H, ketal); 3.80 s (3H, OMe); 3.42 m (3H, methyl); 0.70 s (3H, H-18)

b)

17β-Hydroxy-11β-(4-methoxyphenyl)-17α-methyloestra-4,14-dien-3-one 820 mg of 17β-hydroxy-11β-(4-methoxyphenyl)-17α-methyloestra-4,14-dien-3-one are prepared in the manner described in Example 1 r) from 910 mg of 3,3-[1,2-ethanediylbis(oxy)]-11β-(4-methoxyphenyl)-17α-methyloestra-5,14-dien-17β-ol in 25 ml of acetone and 1.5 ml of 4 molar aqueous hydrochloric acid.

$^1$H-NMR (CDCl$_3$): δ=7.49 d (J=9 Hz, 2H, Ar); 6.85 d (J=9 Hz, 2H, Ar); 5.88 sbr (1H, H-4); 5.28 m (1H, H-15); 3.80 s (3H, OMe); 3.37 ddbr (J=7, 5 Hz, 1H, H-11); 1.23 s (3H, methyl); 0.80 s ( 3H, H-18 )

[α]$_D^{20}$= +106.2° (CHCl$_3$; c=0.563 ) M.p.=186° C.

EXAMPLE 4

11β-[4-(3-Furanyl)phenyl]-17β-hydroxy-17α-methyloestra-4,14-dien-3-one a)

3,3-[1,2-Ethanediylbis(oxy)]-11β-(4-hydroxyphenyl)-17α-methyloestra-5,14-dien-17β-ol 3.7 g of 3,3-[1,2-ethanediylbis(oxy)]-11β-(4-methoxyphenyl)-17α-methyl-5,14-dien-17β-ol and 2.37 g of sodium methanethiolate in 50 ml of dimethylformamide are reacted in the manner described in Example 1 o).

After working up, the crude product is purified by column chromatography on silica gel with a mixture of hexane/ethyl acetate. 3.57 g of 3,3-[1,2-ethanediylbis(oxy)]-11β-(4-hydroxyphenyl)-17α-methyloestra-5,14-dien-17β-ol are obtained in the form of a white foam.

¹H-NMR (CDCl₃): δ=7.25 d (J=9 Hz, 2H, At); 6.70 d (J=9 Hz, 2H, Ar); 5.58 sbr (1H, H-5); 5.21 m (1H, H-15); 3.85-4.00 m (4H, ketal); 3.42 m (3H, H-11); 1.22 s (3H, C-20); 0.69 s ( 3H, C-18)

b)
3,3-[1,2-Ethanediylbis(oxy)]-17α-methyl-11β-[4-[[(trifluoromethyl)sulphonyl]oxy]phenyl]oestra-5,14-dien-17β-ol 3.57 g of 3,3-[1,2-ethanediylbis(oxy)]-11β-(4-hydroxyphenyl)-17α-methyloestra-5,14-dien-17β-ol, 1.84 ml of trifluoromethanesulphonic acid anhydride and 5.16 g of 4-dimethylaminopyridine in 100 ml of absolute methylene chloride are reacted in the manner described in Example 1 p). Column chromatography on silica gel with a mixture of hexane/ethyl acetate yields 3.7 g of 3,3-[1,2-ethanediylbis(oxy)]-17α-methyl-11β-[4-[[(trifluoromethyl)sulphonyl]oxy]phenyl]oestra-5,14-dien-17β-ol in the form of a white foam.

¹H-NMR (CDCl₃): δ=7.50 d (J=8 Hz, 2H, Ar); 7.18 d (J=8 Hz, 2H, Ar); 5.60 m (1H, H-5); 5.24 m (1H, H-15); 3.85-4.00 m (4H, ketal); 3.50 ddbr (J=5, 6Hz, 1H, H-11); 1.22 s (3H, C-20); 0.62 s (3H, C-18)

c) 3,3-[1,2-Ethanediylbis(oxy)]-11β-[4-( 3-furanyl)phenyl ]-17α-methyloestra-5,14-dien-17β-ol Preparation of (3-furanyl)tributylstannane: 69.5 ml of a 1.6 molar solution of n-butyllithium in hexane are mixed with 60 ml of absolute tetrahydrofuran. The mixture is cooled to −60° C. and 10 ml of 3-bromofuran are added dropwise at such a rate that the internal temperature does not exceed −50° C.. When the addition is complete, the whole is stirred for 15 minutes at −60° C. and then 33.2 ml of tributyltin chloride are added dropwise, during the course of which the internal temperature is not allowed to exceed −50° C.. When the addition is complete, the reaction solution is allowed to come to −10° C. and is then stirred for one hour at that temperature. The solution is then carefully quenched with water. The aqueous phase is extracted with ethyl acetate. The organic phase is washed with saturated sodium chloride solution and dried over sodium sulphate. It is filtered off and the solvent is removed in vacuo. The crude product obtained is purified by distillation in a high vacuum. 30.14 g of (3-furanyl)tributylstannane are obtained in the form of a light-yellow oil (boiling point=100°-104° C. at 0.09 torr).

Coupling: 1.8 g of 3,3-[1,2-ethanediylbis(oxy)]-17α-methyl-11β-[4-[[(trifluoromethyl)sulphonyl]oxy]phenyl]oestra-5,14-dien-17β-ol, 1.51 g of (3-furanyl)tributylstannane, 185 mg of tetrakis(triphenylphosphine)palladium, 275 mg of lithium chloride and 0.34 ml of pyridine are reacted analogously to Example 1 q) in 25 ml of dioxan. The crude product is purified by column chromatography on silica gel with a mixture of hexane/ethyl acetate. 1.15 g of 3,3-[1,2-ethanediylbis(oxy)]-11β-[4-(3-furanyl)phenyl]-17α-methyloestra-5,14-dien-17β-ol are obtained in the form of a white foam.

¹H-NMR (CDCl₃): δ=7.70 dbr (J=1.3 Hz, 1H, Fu-2); 7.48 dd (J=1.8, 1.3 Hz, 1H, Fu-5); 7.40 m (4H, Ar); 6.70 dbr (J=1.8, 1H, Fu-4); 5.60 m (1H, H-6); 5.20 m (1H, H-15); 3.90-4.00 m (4H, ketal); 3.50 ddbr (J=5, 6 Hz, 1H, H-11); 1.20 s (3H, C-20); 0.70 s (3H, C-18)

d)
11β-[4-(3-Furanyl)phenyl]-17β-hydroxy-17α-methyloestra-4,14-dien-3-one 1.15 g of 3,3-[1,2-ethanediylbis(oxy)]-11β-[4-(3-furanyl)phenyl]-17α-methyloestra-5,14-dien-17β-ol and 2.9 ml of 4 normal aqueous hydrochloric acid solution in 60 ml of acetone are reacted in the manner described in Example 1 r). Column chromatography on silica gel with a mixture of hexane/ethyl acetate and recrystallisation from a mixture of diisopropyl ether/hexane yields 794 mg of 11β-[4-(3-furanyl)phenyl]-17β-hydroxy-17α-methyloestra-4,14-dien-3-one in the form of white crystals.

¹H-NMR (CDCl₃): δ=7.73 dbr (1.3 Hz, 1H, Fu-2); 7.45-7.53 m (5H, Ar and Fu-5); 6.70 dbr (J=1.8 Hz, 1H, Fu-4); 5.90 m (1H, H-4); 5.30 m (1H, H-15); 3.41 ddbr (J=5, 6 Hz, 1H, H-11); 1.22 s (3H, C-20); 0.80 s (3H, C-18)

$[\alpha]_D^{20}$ = +153° (CHCl₃; c=0.510) M.p.=198°-9° C.

EXAMPLE 5

11β-(4-Acetylphenyl)-17β-hydroxy-17α-methyloestra-4,14-dien-3-one a)
3,3-[1,2-Ethanediylbis(oxy)]-11β-[4-(1-ethoxyethenyl)-phenyl]-17α-methyloestra-5,14-dien-17β-ol 1.8 g of 3,3-[1,2-ethanediylbis(oxy)]-17α-methyl-11β-[4-[[(trifluoromethyl)sulphonyl]oxy]phenyl]oestra-5,14-dien-17β-ol, 1.43 ml of (1-ethoxyvinyl)tributyltin, 185 mg of tetrakis(triphenylphosphine)palladium, 275 mg of lithium chloride and 0.34 ml of pyridine are reacted in 25 ml of dioxan in the manner described in Example 1 q). 1.31 g of 3,3-[1,2-ethanediylbis(oxy)]-11β-[4-(1-ethoxyethenyl)phenyl]-17α-methyloestra-5,14-dien-17β-ol is obtained, which is used in the next step without being purified.

b)
11β-(4-Acetylphenyl)-17β-hydroxy-17α-methyloestra-4,14-dien-3-one

Starting from 1.31 g of 3,3-[1,2-ethanediylbis(oxy)]-11β-[4-(1-ethoxyethenyl)phenyl]-17α-methyloestra-5,14-dien-17β-ol and 3.3 ml of 4 normal aqueous hydrochloric acid in 65 ml of acetone, there are obtained analogously to Example 1 r), after column chromatography on silica gel with a mixture of hexane/ethyl acetate and crystallisation from diisopropyl ether/acetone, 860 mg of 11β-(4-acetylphenyl)-17β-hydroxy-17α-methyloestra-4,14-dien-3-one in the form of white crystals.

¹H-NMR (CDCl₃): δ=7.92 d (J=8 Hz, 2H, Ar); 7.61 d (J=8 Hz, 2H, Ar); 5.90 m (1H, H-4); 5.30 m (1H, H-14); 3.49 ddbr (J=5, 6 Hz, 1H, H-11); 2.60 s (3H, acetyl); 1.23 s (3H, C-20); 0.73 s (3H, C-18)

$[\alpha]_D^{20}$ = +145 3 ° ( CHCl₃; c=0.525) M.p.=195.1° C.

EXAMPLE 6

17β-Hydroxy-17α-methyl-11β-[4-(3-thienyl)phenyl]-oestra-4,14-dien-3-one a)
3,3-[1,2-Ethanediylbis(oxy)]-17α-methyl-11β-[4-(3-thienyl)phenyl]oestra-5,14-dien-17β-ol Preparation of (3-thienyl)tributylstannane: 52.1 g of (3-thienyl)tributylstannane are prepared in 100 ml of tetrahydrofuran analogously to Example 4 c) from 15 ml of 3-bromothiophene and 100 ml of a 1.6 molar solution of butyllithium in hexane and also 38.94 ml of tributyltin chloride. Starting from 920 mg of 3,3-[1,2-ethanediylbis(oxy)]-17α-methyl-11β-[4-[[(trifluoromethyl)sulphonyl]oxy]phenyl]oestra-5,14-dien-17β-ol, 805 mg of (3-thienyl)tributylstannane, 94 mg of tetrakis(triphenylphosphine)palladium, 141 mg of lithium chloride and 0.18 ml of pyridine in 25 ml of dioxan, there are obtained analogously to Example 1 q), after column chromatography on silica gel with a mixture of hexane/ethyl acetate, 420 mg of 3,3-[1,2-ethanediylbis(oxy)]-17α-methyl-11β-[4'(3-thienyl)phenyl]oestra-5,14-dien-17β-ol in the form of a white foam.

b)
17β-Hydroxy-17α-methyl-11β-[4-(3-thienyl)phenyl]oestra-4,14-dien-3-one

Starting from 420 mg of 3,3-[1,2-ethanediylbis(oxy)]-17α-methyl-11β-[4-(3-thienyl)phenyl]oestra-5,14-dien-17β-ol and 1.25 ml of 4 normal aqueous hydrochloric acid in 25 ml of acetone, there are obtained analogously to Example 1 r), after chromatography on silica gel with a mixture of hexane/ethyl acetate and recrystallisation from diisopropyl ether, 250 mg of 17β-hydroxy-17α-methyl-11β-[4-(3-thienyl)phenyl]-oestra-4,14-dien-3-one in the form of white crystals.

$^1$H-NMR (CDCl$_3$): δ=7.52 m (4H, Ar); 7.46 dd (J=4.5, 2.5 Hz, 1H, Th-5); 7.40 dbr (J=2.5 Hz, 1H, Th-2); 7.26 dbr (J=4.5 Hz, 1H, Th-4); 5.90 sbr (1H, H-4); 5.30 m (1H, H-15); 3.45 ddbr (J=5, 6 Hz, 1H, H-11); 1.25 s (3H, C-20); 0.80 s (3H, C-18).

$[\alpha]_D^{20}$ = +170.5° ( CHCl$_3$; c=0.520) M.p.=182°-0° C.

EXAMPLE 7

17β-Hydroxy-11β-(4-methoxyphenyl)-17α-methyloestra-4,15-dien-3-one a)
3,3-[1,2-Ethanediylbis(oxy)]-11β-(4-methoxyphenyl)-17α-methyloestra-5,15-dien-17β-ol 30 ml of a 1.6 molar solution of methyllithium in diethyl ether are diluted with 70 ml of absolute tetrahydrofuran. The whole is cooled to 0° C. and a solution of 4 g of 3,3-[1,2-ethanediylbis(oxy)]-11β-(4-methoxyphenyl)oestra-5,15-dien-17-one in 30 ml of tetrahydrofuran is slowly added dropwise thereto. The whole is then stirred for 1 hour at 0° C. The reaction solution is then poured onto saturated sodium hydrogen carbonate solution and extracted repeatedly with ethyl acetate. The combined organic phases are washed with saturated aqueous sodium chloride solution, dried over sodium sulphate and concentrated in vacuo. 4.15 g of 3,3-[1,2-ethanediylbis(oxy)]-11β-(4-methoxyphenyl)-17α-methyloestra-5,15-dien-17β-ol is obtained, which is used in the subsequent steps without being purified.

b)
17β-Hydroxy-11β-(4-methoxyphenyl)-17α-methyloestra-4,15-dien-3-one 840 mg of 3,3-[1,2-Ethanediylbis(oxy)]-11β-(4-methoxyphenyl)-17α-methyloestra-5,15-dien-17β-ol and 2.5 ml of 4 normal aqueous hydrochloric acid are reacted in 50 ml of acetone in the manner described in Example 1 r). Column chromatography on silica gel with a mixture of hexane/ethyl acetate and recrystallisation from diisopropyl ether yields 510 mg of 17β-hydroxy-11β-(4-methoxyphenyl)-17α-methyloestra-4,15-dien-3-one in the form of white crystals.

$^1$H-NMR (CDCl$_3$): δ=7.32 d (J=8 Hz, 2H, Ar); 6.81 d (J=8 Hz, 2H, Ar); 5.87 m (2H, H-4, H-16); 5.60 dd (J=5, 2.5 Hz, 1H, H-15); 3.80 s (3H, OMe); 3.40 ddbr (J=5, 6 Hz, 1H, H-11); 1.17 s (3H, C-20); 0.72 s (3H, C-18).

$[\alpha]_D^{20}$ = +51.3° ( CHCl$_3$; c=0.520) M.p.=191.5° C.

EXAMPLE 8

17β-Hydroxy-11β-(4-methoxyphenyl)-17α-(1-propynyl)oestra-4,15-dien-3-one a) 3,3-[1,2-Ethanediylbis(oxy)]-11β-(4-methoxyphenyl)-17α-(1-propynyl)oestra-5,15-dien-17β-ol 100 ml of absolute tetrahydrofuran are saturated for 30 minutes at 0° C. with propyne gas. 12.5 ml of a 1.6 molar solution of butyllithium in n-hexane are then added dropwise thereto and the whole is subsequently stirred for 30 minutes. A solution of 840 mg of 3,3-[1,2-ethanediylbis(oxy)]-11β-(4-methoxyphenyl)-17α-methyloestra-5,15-dien-17β-ol in 20 ml of absolute tetrahydrofuran is then added dropwise. The whole is then stirred for a further 1.5 hours at 0° C., subsequently quenched with saturated aqueous ammonium chloride solution and extracted with ethyl acetate. The organic phase is washed with saturated aqueous sodium chloride solution and dried over sodium sulphate. The solvent is removed in vacuo and 920 mg of 3,3-[1,2-ethanediylbis(oxy)]-11β-(4-methoxyphenyl)-17α-(1-propynyl)oestra-5,15-dien-17β-ol are obtained, which is used in the subsequent step without being purified.

$^1$H-NMR (CDCl$_3$): δ=7.24 d (J=8 Hz, 2H, Ar); 6.79 d (J=8 Hz, 2H, Ar ); 5.98 dbr ( J=5 Hz, 1H, H-16); 5.66 dd ( J=5, 2.5 Hz, 1H, H-15); 5.52 m (1H, H-6); 3.90–4.00 m (4H, ketal); 3.80 s (3H, OMe); 3.50 ddbr (J=5, 7 Hz, 1H, H-11); 1.90 s (3H, propyne); 0.69 s (H, C-18)

b)
17β-Hydroxy-11β-(4-methoxyphenyl)-17α-(1-propynyl)oestra-4,15-dien-3-one 920 mg of 3,3-[1,2-ethanediylbis(oxy)]-11β-(4-methoxyphenyl)-17α-(1-propynyl)oestra-5,15-dien-17β-ol and 2.5 ml of 4 normal aqueous hydrochloric acid are reacted in 50 ml of acetone in the manner described in Example 1 r). Column chromatography on silica gel with a mixture of hexane/ethyl acetate and recrystallisation from diisopropyl ether yields 691 mg of 17β-hydroxy-11β-(4-methoxyphenyl)-17α-(1-propynyl)oestra-4,15-dien-3-one in the form of white crystals.

$^1$H-NMR (CDCl$_3$): δ=7.31 d (J=8 HZ, 2H, Ar); 6.81 d (J=8 Hz, 2H, Ar); 6.00 dbr (J=5 Hz, 1H, H-16); 5.87 sbr (1H, H-4); 5.69 dd (J=5, 2.5 Hz, 1H, H-15); 3.80 s (3H, OMe); 3.42 ddbr (J=5, 7 Hz, 1H, H-11); 1.90 s (3H, propyne); 0.73 s (3H, C-18).

$[\alpha]_D^{20}$ = +170° ( CHCl$_3$; c=0.510) M.p.=191.5° C.

EXAMPLE 9

(Z)-17β-Hydroxy-17α-(3-hydroxy-1-propenyl)-11β-(4-methoxyphenyl)oestra-4,15-dien-3-one a)

3,3-[1,2-Ethanediylbis(oxy)]-11β-(4-methoxyphenyl)-17α-[3-[(tetrahydro-2H-pyran-2-yl)oxy]-1-propynyl]-oestra-5,15-dien-178-ol 840 mg of 3,3-[1,2-ethanediylbis(oxy)]-11β-(4-methoxyphenyl)-17α-methyloestra-5,15-dien-17β-ol, 2.18 ml of 3-[(tetrahydro-2H-pyran-2-yl)oxy]-1-propyne and 12.5 ml of a 1.6 molar solution of butyllithium in hexane are reacted in 100 ml of absolute tetrahydrofuran in the manner described in Example 1 m). Column chromatography on silica gel with a mixture of hexane/ethyl acetate yields 1.05 g of 3,3-[1,2-ethanediylbis(oxy)]-11β-(4-methoxyphenyl)-17α-[3-[(tetrahydro-2H-pyran-2-yl)oxy]-1-propynyl]-oestra-5,15-dien-17β-ol in the form of a white foam.

$^1$H-NMR (CDCl$_3$): δ=(mixture of isomeric THP ethers) 7.21 d (J=8 Hz, 2H, Ar); 6.79 d (J=8 Hz, 2H, At); 6.00 dbr (J=6 Hz, 1H, H-16); 5.67 dd (J=6, 2.5 Hz, 1H, H-15); 5.55 m (1H, H-6); 4.62 m (1H, THP); 4.38 m (2H, CH$_2$OTHP); 3.80–4.00 m (4H, ketal); 3.80 s (3H, OMe); 3.50–3.60 m (2H, THP); 0.70 (3H, C-18)

b)

17β-Hydroxy-11β-(4-methoxyphenyl)-17α-[3-[(tetrahydro-2H-pyran-2-yl)oxy]-1-propynyl]oestra-4,15-dien-3-one 1.05 g of 3,3-[1,2-ethanediylbis(oxy)]-11β-(4-methoxyphenyl)-17α-[3-[(tetrahydro-2H-pyran-2-yl)oxy]-1-propynyl]-oestra-5,15-dien-17β-ol and 2.5 ml of 4 normal aqueous hydrochloric acid are reacted in 50 ml of acetone in the manner described in Example 1 r). Column chromatography on silica gel with a mixture of hexane/ethyl acetate yields 690 mg of 17β-hydroxy-11β-(4-methoxyphenyl)-17α-[3-[(tetrahydro-2H-pyran-2-yl)oxy]-1-propynyl]oestra-4,15-dien-3-one in the form of a white foam.

$^1$H-NMR (CDCl$_3$): δ=7.31 d (J=8 Hz, 2H, Ar); 6.82 d (J=8 Hz, 2H, Ar); 6.03 dbr (J=6 Hz, 1H, H-16); 5.88 sbr (1H, H-4); 5.70 dd (J=6, 2.5 Hz, 1H, H-15); 4.38 m (2H, CH$_2$OH); 3.80 s (3H, OMe); 3.41 ddbr (J=5, 6Hz, 1H, H-11); 0.75 s (3H, C-18)

c)

(Z)-17β-Hydroxy-17α-(3-hydroxy-1-propenyl)-11β-(4-methoxyphenyl)oestra-4,15-dien-3-one 690 mg of 17β-hydroxy-11β-(4-methoxyphenyl)-17α-[3-[(tetrahydro-2H-pyran-2-yl)oxy]-1-propynyl]oestra-4,15-dien-3-one are dissolved in 10 ml of tetrahydrofuran. 0.69 ml of pyridine and 69 mg of palladium (10% on barium sulphate) are added. The whole is then hydrogenated for 1 hour under hydrogen. The reaction solution is subsequently filtered through Celite and concentrated in vacuo. column chromatography on silica gel with a mixture of hexane/ethyl acetate yields 500 mg of (Z)-17β-Hydroxy-17α-(3-hydroxy-1-propenyl)-11β-(4-methoxyphenyl)oestra-4,15-dien-3-one in the form of a white foam.

$^1$H-NMR (CDCl$_3$): δ=7.30 d (J=8 Hz, 2H, Ar); 6.80 d (J=8 HZ, 2H, Ar); 5.99 d (J=6 Hz, 1H, H-16); 5.89 sbr (1H, H-4); 5.71 ddd (J=12, 5.5, 5 Hz, 1H, HC=); 5.69 dd (J=6, 2.5 Hz, 1H, H-15); 5.54 dbr (J=12 Hz, 1H, HC=); 4.25 m (2H, CH$_2$OH); 3.80 s (3H, OMe); 3.38 ddbr (J=5, 7Hz, 1H, H-11); 0.80 s (3H, C-20)

EXAMPLE 10

11β-(4-Acetylphenyl)-17β-hydroxy-17α-methyloestra-4,15-dien-3-one a)

3,3-[1,2-Ethanediylbis(oxy)]-11β-(4-hydroxyphenyl)-17α-methyloestra-5,15-dien-17β-ol 4.15 g of 3,3-[1,2-ethanediylbis(oxy)]-11β-(4-methoxyphenyl)-17α-methyloestra-5,15-dien-17β-ol and 2.66 g of sodium methanethiolate are reacted in 50 ml of dimethylformamide in the manner described in Example 1 o). Column chromatography on silica gel with a mixture of hexane/ethyl acetate yields 3.5 g of 3,3-[1,2-ethanediylbis(oxy)]-11β-(4-hydroxyphenyl)-17α-methyloestra-5,15-dien-17β-ol in the form of a white foam.

$^1$H-NMR (CDCl$_3$): δ=7.15 d (J=8 Hz, 2H, Ar); 6.70 d (J=8 Hz, 2H, Ar); 5.84 dbr (J=6 Hz, 1H, H-16); 5.53 dd (J=6, 2.5 Hz, 1H, H-15); 3.90–4.05 m (4H, ketal); 3.40 ddbr (J=5, 7 Hz, 1H, H-11); 3.35 sbr (1H, phenol); 1.12 s (3H, C-20); 0.70 s (3H, C-18)

b)

3,3-[1,2-Ethanediylbis(oxy)]-17α-methyl-11β-[4-[[(1,1,2,2,3,3,4,4,4-nonafluorobutyl)sulphonyl]oxy]phenyl]oestra-5,15-dien-17β-ol 5.5 ml of a 1.6 molar solution of butyllithium in hexane are added dropwise to 3.22 g of 3,3-[1,2-ethanediylbis(oxy)]-11β-(4-hydroxyphenyl)-17α-methyl-5,15-dien-17β-ol in 140 ml of absolute tetrahydrofuran at 0° C. The whole is then stirred at 0° C. for 30 minutes after which 3.04 ml of nonafluorobutanesulphonyl fluoride are added dropwise. The whole is then allowed to come to room temperature over a period of 2 hours and the reaction solution is subsequently poured onto ice-cold saturated sodium hydrogen carbonate solution. The whole is then stirred for a further hour, after which it is extracted with ethyl acetate. The organic phase is washed with saturated aqueous sodium chloride solution, dried over sodium sulphate and concentrated in vacuo. The crude product is purified by column chromatography on silica gel with a mixture of hexane/ethyl acetate. 4.4 g of 3,3-[1,2-ethanediylbis(oxy)]-17α-methyl-11β-[4-[[(1,1,2,2,3,3,4,4,4-nonafluorobutyl)sulphonyl]oxy]phenyl]oestra-5,15-dien-17β-ol are obtained in the form of a white foam.

$^1$H-NMR (CDCl$_3$): δ=7.43 d (J=8 Hz, 2H, Ar); 7.17 d (J=8 Hz, 2H, Ar); 5.85 dbr (J=6 Hz, 1H, H-16); 5.57 dd (J=6, 2.5 Hz, 1H, H-15); 3.90–4.05 m (4H, ketal); 3.55 ddbr (J=5, 7 Hz, 1H, H-11); 1.15 s (3H, C-20); 0.62 s (3H, C-18)

c)

3,3-[1,2-Ethanediylbis(oxy)]-11β-[4-(1-ethoxyethenyl)-phenyl]-17α-methyloestra-5,15-dien-17β-ol 2.26 g of 3,3-[1,2-ethanediylbis(oxy)]-17α-methyl-11β-[4-[[(1,1,2,2,3,3,4,4,4-nonafluorobutyl)sulphonyl-]oxy]phenyl]oestra-5,15-dien-176-ol, 1.43 ml of (1-ethoxyvinyl)tributyltin, 185 mg of tetrakis(triphenylphosphine)palladium, 275 mg of lithium chloride and 0.34 ml of pyridine are reacted in 25 ml of absolute dioxan in the manner described in Example 1 q). The crude product is used in the next step without being purified.

d)

11β-(4-Acetylphenyl)-17β-hydroxy-17α-methyloestra-4,15-dien-3-one 1.37 g of 3,3-[1,2-ethanediylbis(oxy)]-11β-[4-(1-ethoxyethenyl)phenyl]-17α-methyloestra-5,15-dien-17β-ol and 3 ml of 4 normal aqueous hydrochloric acid are reacted in 75 ml of acetone in the manner described in Example 1 r). Column chromatography on silica gel with a mixture of hexane/ethyl acetate and recrystallisation from diisopropyl ether yields 700 mg of 11β-(4-acetylphenyl)-17β-hydroxy-17α-methyloestra-4,15-dien-3-one in the form of white crystals.

$^1$H-NMR (CDCl$_3$): δ=7.90 d (J=8 Hz, 1H, At); 7.52 d (J=8 Hz, 1H, Ar); 5.90 m (2H, H-4, H-16); 5.60 dd (J=6, 2.5 Hz, 1H, H-15); 3.50 ddbr (J=5, 7 Hz, 1H, H-11); 2.60 s (3H, acetyl); 1.20 s (3H, C-20); 0.70 s (3H, C-18)

[α]$_D^{20}$= +89.5° (CHCl$_3$; c=0.505) M.p.=223.7° C.

EXAMPLE 11

11β-[4-(3-Furanyl)phenyl]-17β-hydroxy-17α-methyloestra-4,15-dien-3-one a) 3,3-[1,2-Ethanediylbis(oxy)]-11β-[4-(3-furanyl)phenyl]-17α-methyloestra-5,15-dien-17β-ol 705 mg of 3,3-[1,2-ethanediylbis(oxy)]-17α-methyl-11β-[4-[[(1,1,2,2,3,3,4,4,4-nonafluorobutyl)sulphonyl]oxy]phenyl]oestra-5,15-dien-17β-ol, 0.58 g of (3-furanyl)tributylstannane, 60 mg of tetrakis(triphenylphosphine)palladium and 85 mg of lithium chloride are reacted in 10 ml of dioxan in the manner described in Example 1 q). Column chromatography on silica gel with a mixture of hexane/ethyl acetate yields 320 mg of 3,3-[1,2-ethanediylbis(oxy)]-11β-[4-(3-furanyl)phenyl]-17α-methyloestra-5,15-dien-17β-ol in the form of a white foam.

$^1$H-NMR (CDCl$_3$): δ=7.72 dbr (J=1.3 Hz, 1H, Fu-2); 7.48 dd (J=1.8, 1.3 Hz, 1H, Fu-5); 7.35–7.43 m (4H, Ar); 6.70 dbr (J=1.8 Hz, 1H, Fu-4); 5.87 dbr (J=6 Hz, 1H, H-16); 5.52–5.60 m (2H, H-15, H-6); 3.90–4.00 m (4H, ketal); 3.53 ddbr (J=5, 7 Hz, 1H, H-11); 1.28 s (3H, C-20); 0.70 s (3H, C-18)

b)

11β-[4-(3-Furanyl)phenyl]-17β-hydroxy-17α-methyloestra-4,15-dien-3-one 1.32 g of 3,3-[1,2-ethanediylbis(oxy)]-11β-[4-(3-furanyl)phenyl]-17α-methyloestra-5,15-dien-17β-ol and 3 ml of 4 normal aqueous hydrochloric acid are reacted in 75 ml of acetone in the manner described in Example 1 r). Column chromatography on silica gel with a mixture of hexane/ethyl acetate and recrystallisation from diisopropyl ether yields 894 mg of 11β-[4-(3-furanyl)phenyl]-17β-hydroxy-17α-methyloestra-4,15-dien-3-one in the form of white crystals.

$^1$H-NMR (CDCl$_3$): δ=7.72 dbr (J=1.3 Hz, 1H, Fu-2); 7.49 dd (1.8, 1.3 Hz, 1H, Fu-5); 7.40–7.44 m (4H, Ar); 6.70 dbr (J=1.8 Hz, 1H, Fu-4); 5.89 m (2H, H-4, H-16); 5.60 dd (J=6, 2.5 Hz, 1H, H-15); 3.47 ddbr (J=5, 7 Hz, 1H, H-11); 1.20 s (3H, C-20); 0.80 s (3H, C-18)

[α]$_D^{20}$= +111.4° (CHCl$_3$; c=0.515) M.p.=178.9° C.

EXAMPLE 12

17β-Hydroxy-17α-methyl-11β-[4-(3-pyridinyl)phenyl]oestra-4,15-dien-3-one a)

3,3-[1,2-Ethanediylbis(oxy)]-17α-methyl-11β-[4-(3-pyridinyl)phenyl]oestra-5,15-dien-17β-ol 1.3 g of 3,3-[1,2-ethanediylbis(oxy)]-17α-methyl-11β-[4-[[(1,1,2,2,3,3,4,4,4-nonafluorobutyl)sulphonyl]oxy]phenyl]oestra-5,15-dien-17β-ol, 310 mg of diethyl-(3-pyridinyl)borane, 110 mg of tetrakis(triphenylphosphine)palladium, 160 mg of lithium chloride and 2.4 ml of a 2 molar aqueous sodium carbonate solution are reacted in 15 ml of toluene and 7 ml of ethanol in the manner described in Example 2a). Column chromatography on silica gel with a mixture of hexane/ethyl acetate yields 890 mg of 3,3-[1,2-ethanediylbis(oxy)]-17α-methyl-11β-[4-(3-pyridinyl)phenyl]oestra-5,15-dien-17β-ol in the form of a white foam.

$^1$H-NMR (CDCl$_3$): δ=8.87 sbr (1H, Py); 8.67 dbr (J=4.5 Hz, 1H, Py); 7.90 dtr (7.5, 1 Hz, 1H, Py); 7.68 m (1H, Ar); 7.45–7.55 m (3H, Ar); 7.35 dd (J=7.5, 4.5 Hz, 1H, Py); 5.89 dbr (J=6 Hz, 1H, H-16); 5.55–5.62 m (2H, H-6, H-15); 3.90–4.00 m (4H, ketal); 3.60 ddbr (J=5, 7 Hz, 1H, H-11); 1.90 s (3H, C-20); 0.73 s (3H, C-18)

b)

17β-Hydroxy-17α-methyl-11β-[4-(3-pyridinyl)phenyl]oestra-4,15-dien-3-one 890 mg of 3,3-[1,2-ethanediylbis(oxy)]-17α-methyl-11β-[4-(3-pyridinyl)phenyl]oestra-5,15-dien-17β-ol and 3.2 ml of 4 normal aqueous hydrochloric acid are reacted in 65 ml of acetone in the manner described in Example 1 r). Column chromatography on silica gel with a mixture of hexane/ethyl acetate and recrystallisation from a mixture of diisopropyl ether/ethyl acetate yields 550 mg of 17β-hydroxy-17α-methyl-11β-[4-(3-pyridinyl)phenyl]oestra-4,15-dien-3-one in the form of white crystals.

$^1$H-NMR (CDCl$_3$): δ=8.88 sbr (1H, Py); 8.60 dbr (J=4.5 Hz, 1H, Py); 7.90 dtr (7.5, 1 Hz, 1H, Py); 7.70 m (1H, Ar); 7.50–7.60 m (3H, Ar); 7.36 dd (J=7.5, 4.5 Hz, 1H, Py); 5.90 m (2H, H-4, H-16); 5.60 dd (J=6, 2.5 Hz, 1H, H-15); 3.52 ddbr (J=5, 7 Hz, 1H, H-11); 1.20 s (3H, C-20); 0.78 s (3H, C-18)

[α]$_D^{20}$= 113.9 (CHCl$_3$; c=0.510) M.p.=158.6° C.

EXAMPLE 13

4'-[17β-Hydroxy-17α-methyl-3-oxo-oestra-4,15-dien-11β-yl][1,1'-biphenyl]-4-carbonitrile a)

4'-[3,3-[1,2-Ethanediylbis(oxy)]-17β-hydroxy-17α-methyloestra-5,15-dien-11β-yl][1,1'-biphenyl]-4-carbonitrile 2.4 g of 3,3-[1,2-ethanediylbis(oxy)]-17α-methyl-11β-[4-[[(1,1,2,2,3,3,4,4,4-nonafluorobutyl)sulphonyl]oxy]phenyl]oestra-5,15-dien-17β-ol, 650 mg of (4-cyanophenyl)boronic acid, 200 mg of tetrakis(triphenylphosphine)palladium, 290 mg of lithium chloride and 4.3 ml of a 2 molar aqueous sodium carbonate solution are reacted in 25 ml of toluene and 12 ml of ethanol analogously to Example 2 a). Column chromatography on silica gel with a mixture of hexane/ethyl acetate yields 1.63 g of 4'-[3,3-[1,2-ethanediylbis(oxy)]-17β-hydroxy-17α-methyloestra-5,15-dien-11β-yl][1,1'-biphenyl]-4-carbonitrile in the form of a white foam.

¹H-NMR (CDCl₃): δ=7.70–7.73 m (4H, Ar); 7.45–7.55 m (4H, Ar); 7.88 dbr (J=6 Hz, 1H, H-16); 5.55–5.60 m (2H, H-6, H-15); 3.90–4.00 m (4H, ketal); 3.58 ddbr (J=5, 7 Hz, 1H, H-11); 1.20 s (3H, C-20); 0.70 s (3H, C-18)

b)
4'-[17β-Hydroxy-17α-methyl-3-oxo-oestra-4,15-dien-11β-yl][1,1'-biphenyl]-4-carbonitrile 500 mg of 4'-[3,3-[1,2-ethanediylbis(oxy)]-17β-hydroxy-17α-methyloestra-5,15-dien-11β-yl][1,1'-biphenyl]-4-carbonitrile and 1.25 ml of 4 normal aqueous hydrochloric acid are reacted in 25 ml of acetone analogously to Example 1 r). Column chromatography on silica gel with a mixture of hexane/ethyl acetate and recrystallisation from diisopropyl ether yields 380 mg of 4'-[17β-hydroxy-17α-methyl-3-oxo-oestra-4,15-dien-11β-yl][1,1'-biphenyl]-4-carbonitrile in the form of white crystals.

¹H-NMR (CDCl₃): δ=7.70–7.74 m (4H, Ar); 7.50–7.55 m (4H, Ar); 5.90 m (2H, H-4, H-16); 5.60 dd (J=6, 2.5 Hz, 1H, H-15); 3.62 ddbr (5, 7 Hz, 1H, H-11); 1.20 s (3H, C-20); 0.78 s (3H, C-18)

[α]$_D^{20}$=150.6° (CHCl₃; c=0.515) M.p.=205.5° C.

EXAMPLE 14

4'-17β-Methoxy-17α-methyl-3-oxo-oestra-4,15-dien-11β-yl][1,1'-biphenyl]-4-carbonitrile a)
4'-[3,3-[1,2-Ethanediylbis(oxy)]-17β-methoxy-17α-methyloestra-5,15-dien-11β-yl][1,1'-biphenyl]-4-carbonitrile 500 mg of 4'-[3,3-[1,2-ethanediylbis(oxy)]-17β-hydroxy-17α-methyloestra-5,15-dien-11β-yl][1,1'-biphenyl]-4-carbonitrile, dissolved in 15 ml of absolute tetrahydrofuran, are added at room temperature to a suspension of 120 mg of sodium hydride (60% in paraffin oil) in 5 ml of absolute tetrahydrofuran. Subsequently 0.38 ml of iodomethane are added and the whole is boiled under reflux for 2 hours, then carefully quenched with saturated sodium hydrogen carbonate solution and extracted with ethyl acetate. The organic phase is washed with saturated aqueous sodium chloride solution, dried over sodium sulphate, filtered and concentrated by rotatory evaporation in vacuo. Column chromatography on silica gel with a mixture of hexane/ethyl acetate yields 260 mg of 4'-[3,3-[1,2-ethanediylbis(oxy)]-17β-methoxy-17α-methyloestra-5,15-dien-11β-yl][1,1'-biphenyl]-4-carbonitrile in the form of a white foam.

¹H-NMR (CDCl₃): δ=7.68–7.75 m (4H, Ar); 7.42–7.55 m (4H, Ar); 5.85 dbr (J=6 Hz, 1H, H-16); 5.72 dd (J=6, 2.5 Hz, 1H, H-15); 5.57 m (1H, H-6); 3.90–4.00 m (4H, ketal); 3.55 ddbr (J=5, 7 Hz, 1H, H-11); 3.20 s (3H, OMe); 1.20 s (3H, C-20); 0.70 s (3H, C-18)

b)
4'-17β-Methoxy-17α-methyl-3-oxo-oestra-4,15-dien-11β-yl][1,1'-biphenyl]-4-carbonitrile 260 mg of 4'-[3,3-[1,2-ethanediylbis(oxy)]-17β-methoxy-17α-methyloestra-5,15-dien-11β-yl][1,1'-biphenyl]-4-carbonitrile are reacted with 0.7 ml of 4 normal aqueous hydrochloric acid in 14 ml of acetone in the manner described in Example 1 r). Column chromatography on silica gel with a mixture of hexane/ethyl acetate yields 218 mg of 4'-17β-methoxy-17α-methyl-3-oxo-oestra-4,15-dien-11β-yl][1,1'-biphenyl]-4-carbonitrile in the form of a white foam.

¹H-NMR (CDCl₃): δ=7.70–7.75 m (4H, Ar); 7.50–7.55 m (4H, Ar); 5.90 sbr (1H, H-4); 5.87 dbr (J=6 Hz, 1H, H-16); 5.75 dd (J=6, 2.5 Hz, 1H, H-15); 3.50 ddbr (J=5, 7 Hz, 1H, H-11); 3.20 s (3H, OMe); 1.18 s (3H, C-20); 0.77 s (3H, C-18)

[α]$_D^{20}$=129.6° (CHCl₃; c=0.50)

EXAMPLE 15

4'-[17β-Hydroxy-3-oxo-17α-(1-propynyl)oestra-4,15-dien-11β-yl][1,1'-biphenyl]-4-carbonitrile a)
3,3-[1,2-Ethanediylbis(oxy)]-11β-(4-hydroxyphenyl)oestr-5-en-17-one 20 g of 3,3-[1,2-ethanediylbis(oxy)]-11β-(4-methoxyphenyl)oestr-5-en-17-one and 13.4 g of sodium methanethiolate are reacted in 350 ml of dimethylformamide analogously to Example 1 o). 19 g of 3,3-[1,2-ethanediylbis(oxy)]-11β-(4-hydroxyphenyl)oestr-5-en-17-one are obtained which are used in the subsequent step without being purified.

b)
11β-[4-[[Dimethyl-(1,1-dimethylethyl)silyl]oxy]phenyl]-3,3-[1,2-ethanediylbis(oxy)]oestr-5-en-17-one 8.9 g of 3,3-[1,2-ethanediylbis(oxy)]-11β-(4-hydroxyphenyl)oestr-5-en-17-one are dissolved in 90 ml of dimethylformamide. 4.63 g of imidazole and 4.93 g of dimethyl-(1,1-dimethylethyl)silyl chloride are added and the whole is stirred at room temperature for 4 hours. The reaction solution is then poured onto ice-water and extracted with ethyl acetate. The organic phase is washed with saturated aqueous sodium chloride solution, filtered and concentrated in vacuo. The crude product obtained is purified by column chromatography on silica gel with a mixture of hexane/ethyl acetate. 10.27 g of 11β-[4-[[dimethyl-(1,1-dimethylethyl)silyl]oxy]phenyl]-3,3-[1,2-ethanediylbis(oxy)]oestr-5-en-17-one are obtained in the form of a white foam.

¹H-NMR (CDCl₃): δ=7.09 d (J=8 Hz, 2H, At); 6.63 d (J=8 Hz, 2H, Ar); 5.46–5.48 m (1H, H-6) 3.80–3.90 m (4H, ketal); 3.30 ddbr (J=5, 7 Hz, 1H, H-11); 1.95 s (3H, propyne); 0.88 s (9H, t-Bu); 0.10 s (6H, SiMe₂)

c) 11β-[4-[[Dimethyl-(1,1-dimethylethyl)silyl]oxy]phenyl]-3,3-[1,2-ethanediylbis(oxy)]-17-[(trimethylsilyl)oxy]oestra-5,16-diene Starting from 6 g of 11β-[4-[[dimethyl-(1,1-dimethylethyl)silyl]oxy]phenyl]-3,3-[1,2-ethanediylbis(oxy)]oestr-5-en-17-one, 4.02 ml of diisopropylamine, 18.13 ml of a 1.6 molar solution of butyllithium in hexane and 5.07 ml of trimethylchlorosilane in 250 ml of tetrahydrofuran, there are obtained analogously to Example 1 e), after recrystallisation from acetonitrile, 6.5 g of 11β-[4-[[dimethyl-(1,1-dimethylethyl)silyl]oxy]phenyl]-3,3-[1,2-ethanediylbis(oxy)]-17-[(trimethylsilyl)oxy]oestra-5,16-diene.

d) 11β-[4-[[Dimethyl-(1,1-dimethylethyl)silyl]oxy]phenyl]-3,3-[1,2-ethanediylbis(oxy)]oestra-5,15-dien-17one In the manner described in Example 1 f), 1.23 g of 11β-[4-[[dimethyl-(1,1-dimethylethyl)silyl]oxy]phenyl]-3,3-[1,2-ethanediylbis(oxy)]oestra-5,15-dien-17-one are obtained in the form of a white foam from 1.65 g of 11β-[4-[[dimethyl-(1,1-dimethylethyl)silyl]oxy]phenyl]-3,3-[ 1,2-ethanediylbis(oxy)]-17-[(trimethylsilyl)oxy]oestra-5,16-diene and 747 mg of palladium(II) acetate in 60 ml of acetonitrile after column chromatography on silica gel with a mixture of hexane/ethyl acetate.

¹H-NMR (CDCl₃): δ:7.52 dd (J=6, 1 Hz, 1H, H-15); 7.19 d (J=8 Hz, 2H, Ar); 6.73 d (J=7, Hz, 2H, Ar); 5.98 dd (J=8, 2.5 Hz, 1H, H-16); 5.50 m (1H, H-6); 3.90–4.00 m (4H, ketal); 3.50 dd (J=5, 7 Hz, 1H, H-11); 1.98 s (3H, propyne); 0.96 (9H, t-Bu); 0.90 s (3H, C-18); 0.20 s (6H, SiMe₂)

e)
11β-[4-[[Dimethyl-(1,1-dimethylethyl)silyl]oxy]-phenyl]-3,3-[1,2-ethanediylbis(oxy)]-17α-(1-propynyl)oestra-5,15-dien-17β-ol 3.5 g of 11β-[4-[[dimethyl-(1,1-dimethylethyl)silyl]oxy]phenyl]-3,3-[1,2-ethanediylbis(oxy)]oestra-5,15-dien-17-one, 42 ml of a 1.6 molar solution of butyllithium and 350 ml of tetrahydrofuran saturated with propyne are reacted in the manner described in Example 8a). 3.7 g of 11β-[4-[[dimethyl-(1,1-dimethylethyl)-silyl]oxy]phenyl]-3,3-[1,2-ethanediylbis(oxy)]-17α-(1-propynyl)oestra-5,15-dien-17β-ol is obtained, which is used in the subsequent step without being purified.

f)
3,3-[1,2-Ethanediylbis(oxy)]-11β-(4-hydroxyphenyl)-17α-(1-propynyl)oestra-5,15-dien-17β-ol 1.98 g of 11β-[4-[[dimethyl-(1,1-dimethylethyl)silyl]oxy]phenyl]-3,3-[1,2-ethanediylbis(oxy)]-17α-(1-propynyl)oestra-5,15-dien-17β-ol are dissolved in 35 ml of tetrahydrofuran. 2.78 g of tetrabutylammonium fluoride trihydrate are added and the whole is then stirred for 1.5 hours at room temperature. The reaction solution is then poured onto saturated sodium hydrogen carbonate solution and extracted with ethyl acetate. The organic phase is washed with saturated aqueous sodium chloride solution, dried over sodium sulphate, filtered and concentrated in vacuo. Chromatography on silica gel with a mixture of hexane/ethyl acetate yields 1.22 g of 3,3-[1,2-ethanediylbis(oxy)]-11β-(4-hydroxyphenyl)-17α-(1-propynyl)oestra-5,15-dien-17β-ol in the form of a white foam.

¹H-NMR (CDCl₃): δ=7.15 d (J=8 Hz, 2H, Ar); 6.70 d (J=8 Hz, 2H, Ar); 6.00 dbr (J=6 Hz, 1H, H-16); 5.54 dd (J=6, 2.5 Hz, 1H, H-15); 5.53 m (1H, H-6); 3.90–4.00 m (4H, ketal); 3.50 ddbr (J=5, 7 Hz, 1H, H-11); 3.40 s (1H, phenol); 1.98 s (3H, propyne); 0.67 s (3H, C-18)

g) 3,3-[1,2-Ethanediylbis(oxy)]-17α-(1-propynyl)-11β-[4-[[(1,1,2,2,3,3,4,4,4-nonafluorobutyl)sulphonyl]oxy]phenyl]oestra-5,15-dien-17β-ol 1.22 g of 3,3-[1,2-ethanediylbis(oxy)]-11β-(4-hydroxyphenyl)-17α-(1-propynyl)oestra-5,15-dien-17β-ol, 1.9 ml of a 1.6 molar solution of n-butyllithium and 1.09 ml of nonafluorobutanesulphonyl fluoride in 70 ml of tetrahydrofuran are reacted analogously to Example 10 b). Column chromatography on silica gel with a mixture of hexane/ethyl acetate yields 1.7 g of 3,3-[1,2-ethanediylbis(oxy)]-17α-(1-propynyl)-11β-[4-[[(1,1,2,2,3,3,4,4,4nonafluorobutyl)sulphonyl]oxy]phenyl]oestra-5,15-dien-17β-ol in the form of a white foam.

¹H-NMR (CDCl₃): δ=7.40 d (J=8 Hz, 2H, Ar); 7.15 d (J=8 Hz, 2H, Ar); 5.98 dbr (J=6 Hz, 1H, H-16); 5.65 dd (J=6, 2.5 Hz, 1H, H-15); 5.55 m (1H, H-6); 3.90–4.00 (4H, ketal); 3.59 ddbr (J=5, 7 Hz, 1H, H-11); 1.98 s (3H, propyne); 0.61 s (3H, C-18)

h) 4'-[3,3-[1,2-Ethanediylbis(oxy)]-17β-hydroxy-17α-(1-propynyl)oestra-5,15-dien-11β-yl]-[1,1'-biphenyl]-4-carbonitrile 560 mg of 3,3-[1,2-ethanediylbis(oxy)]-17α-(1-propynyl)-11β-[4-[[(1,1,2,2,3,3,4,4,4-nonafluorobutyl)-sulphonyl]oxy]phenyl]oestra-5,15-dien-17β-ol, 172 mg of (4-cyanophenyl)boronic acid, 45 mg of tetrakis(triphenylphosphine)palladium, 65 mg of lithium chloride and 0.96 ml of a 2 molar aqueous sodium carbonate solution are reacted in 7 ml of toluene and 3 ml of ethanol analogously to Example 2 a). Column chromatography on silica gel with a mixture of hexane/ethyl acetate yields 300 mg of 4'-[3,3-[1,2-ethanediylbis(oxy)]-17β-hydroxy-17α-(1-propynyl)oestra-5,15-dien-11β-yl][1,1'-biphenyl]-4-carbonitrile in the form of a white foam.

¹H-NMR (CDCl₃): δ=7.70–7.75 m (4H, Ar); 7.47–7.55 m (4H, Ar); 6.02 dbr (J=6 Hz, 1H, H-16); 5.69 dd (J=6, 2.5 Hz, 1H, H-15); 3.90–4.00 m (4H, ketal); 3.61 ddbr (J=5, 7 Hz, 1H, H-11); 1.98 s (3H, propyne); 0.70 s (3H, C-18)

i)
4'-[17β-Hydroxy-3-oxo-17α-(1-propynyl)oestra-4,15-dien-11β-yl][1,1'-biphenyl]-4-carbonitrile 300 mg of 4'-[3,3-[1,2-ethanediylbis(oxy)]-17β-hydroxy-17α-(1-propynyl)oestra-5,15-dien-11β-yl][1,1'-biphenyl]-4-carbonitrile and 1.2 ml of 4 normal aqueous hydrochloric acid in 20 ml of acetone are reacted analogously to Example 1 r). Column chromatography on silica gel with a mixture of hexane/ethyl acetate yields 240 mg of 4'-[17β-hydroxy-3-oxo-17α-(1-propynyl)oestra-4,15-dien-11β-yl][1,1'-biphenyl]-4-carbonitrile in the form of a white foam.

¹H-NMR (CDCl₃): δ=7.68–7.72 m (4H, Ar); 7.45–7.50 m (4H, Ar); 6.02 dbr (J=6 Hz, 1H, H-16); 5.90 sbr (1H, H-5.71 dd (J=6, 2.5 Hz, 1H, H-15); 3.54 ddbr (J=5, 7 Hz, 1H, H-11); 2.00 s (3H, propyne); 0.78 s (3H, C-18)

$[\alpha]_D^{20} = -89°$ (CHCl₃/methanol; c=0.50)

EXAMPLE 16

11β-[4-(3-Furanyl)phenyl]-17β-hydroxy-17α-(1-propynyl)oestra-4,15-dien-3-one a) 3,3-[1,2-Ethanediylbis(oxy) )]-11β-[4-( 3-furanyl)phenyl ]-17α-( 1-propynyl)oestra-5,15-dien-17β-ol Starting from 560 mg of 3,3-[1,2-ethanediylbis(oxy)]-17α-(1-propynyl)-11β-[4-[[(1,1,2,2,3,3,4,4,4-nonafluorobutyl)sulphonyl]oxy]phenyl]oestra-5,15-dien-17β-ol, 0.58 g of (3-furanyl)tributylstannane, 45 mg of tetrakis(triphenylphosphine)palladium and 65 mg of lithium chloride in 10 ml of dioxan, there are obtained analogously to Example 1 q), after column chromatography on silica gel with a mixture of hexane/ethyl acetate, 286 mg of 3,3-[1,2-ethanediylbis(oxy))]-11β-[4-(3-furanyl)phenyl]-17α-(1-propynyl)oestra-5,15-dien-17β-ol in the form of a white foam.

¹H-NMR (CDCl₃): δ=7.72 dbr (J=1.3 Hz, 1H, Fu-2); 7.48 dd (J=1.8, 1.3 Hz, 1H, Fu-5); 7.30–7.40 m (4H, Ar); 6.70 dbr (J=1.8 Hz, 1H, Fu-4); 6.00 dbr (J=6 Hz, 1H, H-16); 5.68 dd (J=6, 2.5 Hz, 1H, H-15); 5.56 m (1H, H-6); 3.90–4.00 m (4H, ketal); 3.56 ddbr (J=5, 7 Hz, 1H, H-11); 1.91 s (3H, propyne); 0.70 s (3H, C-18)

b)

11β-[4-(3-Furanyl)phenyl]-17β-hydroxy-17α-(1-propynyl)oestra-4,15-dien-3-one 286 mg of 3,3-[1,2-ethanediylbis(oxy)]-11β-[4-(3-furanyl)phenyl]-17α-(1-propynyl)oestra-5,15-dien-17β-ol and 0.45 ml of 4 normal hydrochloric acid are reacted in 10 ml of acetone analogously to Example 1 r). Chromatography on silica gel with a mixture of hexane/ethyl acetate yields 220 mg of 11β-[4-(3-furanyl)phenyl]-17β-hydroxy-17α-(1-propynyl)oestra-4,15-dien-3-one in the form of a white foam.

$^1$H-NMR (CDCl$_3$): δ=7.72 dbr (J=1.3 Hz, 1H, Fu-2); 7.48 dd (J=1.8, 1.3 Hz, 1H, Fu-5); 7.38–7.45 m (4H, Ar); 6.70 dbr (1.8 Hz, 1H, Fu-4); 6.00 dbr (J=6 Hz, 1H, H-15); 5.88 sbr (1H, H-4); 5.70 dd (J=6, 2.5 Hz, 1H, H-15); 3.50 ddbr (J=5, 7 Hz, 1H, H-11); 1.90 s (3H, propyne); 0.71 s (3H, C-18)

EXAMPLE 17

11β-(4-Acetylphenyl)-17β-hydroxy-17α-(1-propynyl)oestra-4,15-dien-3-one a)

3,3-[1,2-Ethanediylbis(oxy)]-11β-[4-(1-ethoxyethenyl)phenyl]-17α-(1-propynyl)oestra-5,15-dien-17β-ol 560 mg of 3,3-[1,2-ethanediylbis(oxy)]-17α-(1-propynyl)-11β-[4-[[(1,1,2,2,3,3,4,4,4-nonafluorobutyl)sulphonyl]oxy]phenyl]oestra-5,15-dien-17β-ol, 0.34 ml of (1ethoxyvinyl)tributyltin, 45 mg of tetrakis(triphenylphosphine)palladium and 65 mg of lithium chloride are reacted in 10 ml of dioxan analogously to Example 1 q). Column chromatography on silica gel with a mixture of hexane/ethyl acetate yields 277 mg of 3,3-[1,2-ethanediylbis(oxy)]-11β-[4-(1-ethoxyethenyl)phenyl]-17α-(1-propynyl)oestra- 5,15-dien-17β-ol in the form of a white foam.

b)

11β-(4-Acetylphenyl)-17β-hydroxy-17α-(1-propynyl)oestra-4,15-dien-3-one 277 mg of 3,3-[1,2-ethanediylbis(oxy)]-11β-[4-(1-ethoxyethenyl)phenyl]-17α-(1-propynyl)oestra-5,15-dien-17β-ol and 0.43 ml of 4 normal aqueous hydrochloric acid are reacted in 10 ml of acetone analogously to Example 1 r). Column chromatography on silica gel with a mixture of hexane/ethyl acetate yields 200 mg of 11β-(4-acetylphenyl)-17β-hydroxy-17α-(1-propynyl)oestra-4,15-dien-3-one in the form of a white foam.

$^1$H-NMR (CDCl$_3$): δ=7.90 d (J=8 Hz, 2H, Ar); 7.52 d (J=8 Hz, 2H, Ar); 6.00 dbr (J=6 Hz, 1H, H-16); 5.90 sbr (1H, H-4) 5.70 dd (J=6, 2.5 Hz, 1H, H-15); 3.54 ddbr (J=5, 7 Hz, 1H, H-11); 1.95 s (3H, propyne); 0.72 s (3H, C-18).

EXAMPLE 18

4'-[4',5'-Dihydro-3-oxospiro[oestra-4,15-diene-17β,2'(3'H)-furan ]-11β-yl][1,1 '-biphenyl ]-4-carbonitrile a)

3,3-[1,2-Ethanediylbis(oxy)]-11β-(4-methoxyphenyl)-17α-(2-propenyl)oestra-5,15-dien-17β-ol 2 g of 3,3-[1,2-ethanediylbis(oxy)]-11β-(4-methoxyphenyl)oestra-5,15-dien-17-one dissolved in 60 ml of absolute tetrahydrofuran are added dropwise, at 0° C. under argon, to 12 ml of a 2 molar solution of allylmagnesium chloride in tetrahydrofuran. The whole is subsequently stirred at 0° C. for 30 minutes, and then quenched with saturated ammonium chloride solution and extracted with ethyl acetate. The organic phase is washed with saturated aqueous sodium chloride solution, dried over sodium sulphate, filtered and concentrated in vacuo. Column chromatography on silica gel with a mixture of hexane/ethyl acetate yields 1.58 g of 3,3-[1,2-ethanediylbis(oxy)]-11β-(4-methoxyphenyl)-17α-(2-propenyl)oestra-5,15-dien-17β-ol in the form of a white foam.

$^1$H-NMR (CDCl$_3$): δ=7.23 d (J=8 Hz, 2H, Ar); 6.78 d (J=8 Hz, 2H, Ar); 5.80-5.95 m (2H); 5.55 m (2H); 5.10–5.15 m (2H); 3.90–4.00 m (4H, ketal); 3.80 s (3H, OMe); 3.48 ddbr (J=5, 7 Hz, 1H, H-11); 0.70 s (3H, C-18)

b)

3,3-[1,2-Ethanediylbis(oxy)]-17α-(3-hydroxypropyl)-11β-(4-methoxyphenyl)oestra-5,15-dien-17β-ol 6 ml of a 0.5 molar solution of 9-borabicyclo[3.3.1]nonane in tetrahydrofuran are added under argon to 463 mg of 3,3-[1,2-ethanediylbis(oxy)]-11β-(4-methoxyphenyl)-17α-(2-propenyl)oestra-5,15-dien-17β-ol in 6 ml of absolute tetrahydrofuran. The whole is then stirred for 12 hours at room temperature, 5.3 ml of a 2.5 normal aqueous sodium hydroxide solution and 3.2 ml of 30% hydrogen peroxide are then added, and the whole is boiled under reflux for 1 hour and then allowed to cool and extracted with ethyl acetate. The organic phase is washed with water, saturated sodium thiosulphate solution and saturated sodium chloride solution, dried over sodium sulphate, filtered and concentrated in vacuo. Column chromatography on silica gel with a mixture of hexane/ethyl acetate yields 450 mg of 3,3-[1,2-ethanediylbis(oxy)]-17α-(3-hydroxypropyl)-11β-(4-methoxyphenyl)oestra-5,15-dien-17β-ol.

$^1$H-NMR (CDCl$_3$): δ=7.20 d (J=8 Hz, 2H, Ar); 6.79 d (J=8 Hz, 2H, At); 5.92 dbr (J=7 Hz, 1H, H-16); 5.67 dd (J=7, 2.5 Hz, 1H, H-15); 5.55 m (1H, H-6); 3.90–4.00 m (4H, ketal); 3.65–3.70 m (2H, CH$_2$OH); 3.47 ddbr (J=5, 7 Hz, 1H, H-11); 0.68 s (3H, C-18)

c)

4-[4',5'-Dihydro-3,3-[1,2-ethanediylbis(oxy)]spiro[oestra-5,15-diene-17β,2'(3'H)-furan]-11β-yl]phenol Starting from 2.24 g of 3,3-[1,2-ethanediylbis(oxy)]-17α-(3-hydroxypropyl)-11β-(4-methoxyphenyl)oestra-5,15-dien-17β-ol and 1.34 g of sodium methanethiolate in 30 ml of dimethylformamide, there are obtained analogously to Example 1 o), after column chromatography on silica gel with a mixture of hexane/ethyl acetate, 1.25 g of 4-[4',5'-dihydro-3,3-[1,2-ethanediylbis(oxy)]spiro[oestra-5,15-diene-17β,2'(3'H)-furan]-11β-yl]phenol.

$^1$H-NMR (CDCl$_3$): δ=7.15 d (J=8 Hz, 2H, At); 6.70 d (J=8 Hz, 2H, At); 5.83 dbr (J=7 Hz, 1H, H-16); 5.65 dd (J=7, 2.5 Hz, 1H, H-15); 5.55 m (1H, H-6); 5.40 s (1H, phenol); 3.90–4.00 m (4H, ketal); 3.75–3.83 m (2H, CH$_2$OH); 3.43 ddbr (J=5, 7 Hz, 1H, H-11); 0.71 s (3H, C-18)

d)

4',5'-Dihydro-3,3-[1,2-ethanediylbis(oxy)]-11β-[4-[[(1,1,2,2,3,3,4,4,4-nonafluorobutyl)sulphonyl]oxy]phenyl]spiro[oestra-5,15-diene-17β,2'(3'H)-furan]

1.25 g of 4-[4',5'-dihydro-3,3-[1,2-ethanediylbis(oxy)]-spiro[oestra-5,15-diene-17β,2'(3'H)-furan]-11β-yl]phenol, 1.9 ml of a 1.6 molar solution of butyllithium in hexane and 0.84 ml of nonafluorobutanesulphonyl fluoride are reacted in 70 ml of absolute tetrahydrofuran analogously to Example 10 b) 19 g of 4',5'-dihydro-3,3-[1,2-ethanediylbis(oxy)]-11β-[4-[[(1,1,2,2,3,3,4,4,4-nonafluorobutyl)sulphonyl]oxy]phenyl]spiro[oestra-5,15-diene-17β,2'(3'H)-furan]is obtained, which is used in the subsequent step without being purified.

e)
4'-[4',5'-Dihydro-3,3-[1,2-ethanediylbis(oxy)]spiro[oestra-5,15-diene-17β,2'(3'H)-furan]-11β-yl][1,1'-biphenyl]-4-carbonitrile Starting from 2.04 g of 4',5'-dihydro-3,3-[1,2-ethanediylbis(oxy)]-11β-[4-[[(1,1,2,2,3,3,4,4,4-nonafluorobutyl)sulphonyl]oxy]phenyl]spiro[oestra-5,15-diene-7β,2'(3'H)-furan], 590 mg of (4-cyanophenyl)boronic acid, 161 mg of tetrakis(triphenylphosphine)palladium, 237 mg of lithium chloride and 3.5 ml of a 2 molar aqueous sodium carbonate solution in 21 ml of toluene and 9 ml of ethanol, there are obtained analogously to Example 2 a), after column chromatography on silica gel with a mixture of hexane/ethyl acetate, 1.16 g of 4'-[4',5'-dihydro-3,3-[1,2-ethanediylbis(oxy)]-spiro[oestra-5,15-diene-17β,2'(3'H)-furan]-11β-yl][1,1'-biphenyl]-4-carbonitrile in the form of a white foam.

$^1$H-NMR (CDCl$_3$): δ=7.70–7.75 m (4H, Ar); 7.45–7.55 m (4H, Ar); 5.87 dbr (J=7 Hz, 1H, H-16); 5.67 dd (J=7, 2.5 Hz, 1H, H-15); 5.50 m (1H, H-6); 3.90–4.00 m (4H, ketal); 3.73–3.80 m (2H, CH$_2$O); 3.54 ddbr (J=5, 7 Hz, 1H, H-11); 0.73 s (3H, C-18)

f)
4'-[4',5'-Dihydro-3-oxospiro[oestra-4,15-diene-17β,2'(3'H)-furan]-11β-yl][1,1'-biphenyl]-4-carbonitrile 1.16 g of 4'-[4',5'-dihydro-3,3-[1,2-ethanediylbis(oxy)]spiro[oestra-5,15-diene-17β,2'(3'H)-furan]-11β-yl][1,1'-biphenyl]-4-carbonitrile and 2.9 ml of 4 normal aqueous hydrochloric acid are reacted in 60 ml of acetone analogously to Example 1 r). Column chromatography on silica gel with a mixture of hexane/ethyl acetate yields 850 mg of 4'-[4',5'-dihydro-3-oxospiro[oestra-4,15-diene-17β,2'(3'H)-furan]-11β-yl][1,1'-biphenyl]-4-carbonitrile in the form of a white foam.

$^1$H-NMR (CDCl$_3$): δ=7.68–7.75 m (4H, Ar); 7.50–7.53 m (4H, Ar); 5.90 sbr (1H, H-4); 5.89 dbr (J=7 Hz, 1H, H-16); 5.70 dd (J=7, 2.5 Hz, 1H, H-15); 3.73–3.80 m (2H, CH$_2$O); 3.50 ddbr (J=5, 7 Hz, 1H, H-11); 0.80 s (3H, C-18)

$[α]_D^{20}$ = +87.8° (CHCl$_3$; c=0.510)

EXAMPLE 19

4'-[17α-Ethynyl-17β-hydroxy-3-oxo-oestra-4,15-dien-11β-yl][1,1'-biphenyl]-4-carbonitrile a)
11β-[4-[[Dimethyl-(1,1-dimethylethyl)silyl]oxy]-phenyl]-3,3-[1,2-ethanediylbis(oxy)]-17α-ethynyloestra-5,15-dien-17β-ol 2.5 g of 11β-[4-[[dimethyl-(1,1-dimethylethyl)silyl]oxy]phenyl]-3,3-[1,2-ethanediylbis(oxy)]oestra-5,15-dien-17-one, 30 ml of a 1.6 molar solution of n-butyllithium in hexane and 250 ml of ethyne-saturated tetrahydrofuran are reacted in the manner described in Example 8a). Column chromatography on silica gel with a mixture of hexane/ethyl acetate yields 2.1 g of 11β-[4-[[dimethyl-(1,1-dimethylethyl)silyl]oxy]phenyl]-3,3-[1,2-ethanediylbis(oxy)]-17α-ethynyloestra-5,15-dien-17β-ol in the form of a white foam.

$^1$H-NMR (CDCl$_3$): δ=7.17 d (J=8 Hz, 2H, Ar); 6.72 d (J=8 Hz, 2H, Ar); 6.04 dbr (J=6 Hz, 1H, H-16); 5.69 dd (J=6, 2.5 Hz, 1H, H-15); 5.53 m (1H, H-6); 3.90–4.00 m (4H, ketal); 3.50 ddbr (J=5, 7 Hz, 1H, H-11); 2.62 s (1H, ethyne); 0.98 s (9H, t-Bu); 0.70 s (3H, C-18); 0.20 s (6H, SiMe$_2$)

b)
3,3-[1,2-Ethanediylbis(oxy)]-17α-ethynyl-11β-(4-hydroxyphenyl)oestra-5,15-dien-17β-ol 2.1 g of 11β-[4-[[Dimethyl(1,1-dimethylethyl)silyl]oxy]phenyl]-3,3-[1,2-ethanediylbis(oxy)]-17α-ethynyloestra-5,15-dien-17β-ol and 3.1 g of tetrabutylammonium fluoride trihydrate are reacted in 60 ml of absolute tetrahydrofuran in the manner described in Example 15f). 1.6 g of 3,3-[1,2-ethanediylbis(oxy)]-17α-ethynyl-11β-(4-hydroxyphenyl)oestra-5,15-dien-17β-ol is obtained, which is used in the subsequent step without being purified.

c)
3,3-[1,2-Ethanediylbis(oxy)]-17α-ethynyl-11β-[4-[[(1,1,2,2,3,3,4,4,4-nonafluorobutyl)sulphonyl]oxy]-phenyl]oestra-5,15-dien-17β-ol 1.46 g of 3,3-[1,2-ethanediylbis(oxy)]-17α-ethynyl-11β-(4-hydroxyphenyl)oestra-5,15-dien-17β-ol, 1.01 ml of nonafluorobutanesulphonyl fluoride and 2.32 ml of a 1.6 molar solution of butyllithium in hexane are reacted in 80 ml of absolute tetrahydrofuran in the manner described in Example 10b). 2.33 g of 3,3-[1,2-ethanediylbis(oxy)]-17α-ethynyl-11β-[4-[[(1,1,2,2,3,3,4,4,4-nonafluorobutyl)sulphonyl]oxy]phenyl]oestra-5,15-dien-17β-ol is obtained, which is used in the subsequent step without being purified.

d)
4'-[3,3-[1,2-Ethanediylbis(oxy)]-17α-ethynyl-17β-hydroxyoestra-5,15-dien-11β-yl][1,1'-biphenyl]-4-carbonitrile 1.3 g of 3,3-[1,2-ethanediylbis(oxy)]-17α-ethynyl-11β-[4-[[(1,1,2,2,3,3,4,4,4-nonafluorobutyl)sulphonyl]oxy]phenyl]oestra-5,15-dien-17β-ol, 384 mg of (4-cyanophenyl)boronic acid, 105 mg of tetrakis(triphenylphosphine)palladium, 155 mg of lithium chloride and 2.3 ml of a 2 molar aqueous sodium carbonate solution are reacted in 15 ml of toluene and 6 ml of ethanol analogously to Example 2 a). Column chromatography on silica gel with a mixture of hexane/ethyl acetate yields 540 mg of 4'-[3,3-[1,2-ethanediylbis(oxy)]-17α-ethynyl-17β-hydroxyoestra-5,15-dien-11β-yl][1,1'-biphenyl]-4-carbonitrile in the form of a white foam.

$^1$H-NMR (CDCl$_3$): δ=7.70–7.75 m (4H, At); 7.45–7.50 m (4H, Ar); 6.05 dbr (J=6 Hz, 1H, H-16); 5.70 dd (J=6, 2.5 Hz, 1H, H-15); 5.58 m (1H, H-6); 3.90–4.00 m (4H, ketal); 3.62 ddbr (J=5, 7 Hz, 1H, H-11); 2.66 s (1H, ethyne); 0.72 s (3H, C-18)

e)
4'-[17α-Ethynyl-17β-hydroxy-3-oxo-oestra-4,15-dien-11β-yl][1,1'-biphenyl]-4-carbonitrile 540 mg of 4'-[3,3-[1,2-ethanediylbis(oxy)]-17α-ethynyl17β-hydroxyoestra-5,15-dien-11β-yl][1,1'-biphenyl]-4-carbonitrile and 1.35 ml of 4 normal aqueous hydrochloric acid are reacted in 30 ml of acetone analogously to Example 1 r). Column chromatography on silica gel with a mixture of hexane/ethyl acetate yields 330 mg of 4'-[17α-ethynyl-17β-hydroxy-3-oxo-oestra-4,15-dien-11β-yl][1,1'-biphenyl]-4-carbonitrile in the form of a white foam.

$^1$H-NMR (CDCl$_3$): δ=7.70–7.75 m (4H, Ar); 7.50–7.55 m (4H, At); 6.07 dbr (J=6 Hz, 1H, H-16); 5.90 sbr (1H, H-4); 5.73 dd (J=6, 2.5 Hz, 1H, H-15); 3.55 ddbr (J=5, 7 Hz, 1H, H-11); 2.70 s (1H, ethyne); 0.80 s (3H, C-18)

TABLE 1

| Test compound | Dose mg/kg/animal p.o. | Abortion rate no. abortions/ total no. | % |
|---|---|---|---|
| B | 1.0 | 4/4 | 100 |
| | 0.3 | 4/4 | 100 |
| | 0.1 | 4/4 | 100 |
| | 0.03 | 1/4 | 25 |
| C | 1.0 | 4/4 | 100 |
| | 0.3 | 4/4 | 100 |
| E | 1.0 | 4/4 | 100 |
| | 0.3 | 4/4 | 100 |
| | 0.1 | 4/4 | 100 |
| | 0.03 | 2/4 | 50 |
| F | 1.0 | 4/4 | 100 |
| | 0.3 | 4/4 | 100 |
| | 0.1 | 4/4 | 100 |
| | 0.03 | 4/4 | 100 |

We claim:

1. Compounds of the general formula I

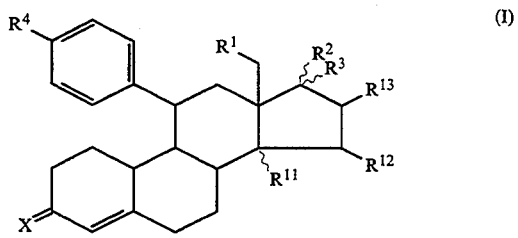

in which either

Ia) R$^{11}$ represents a hydrogen atom in the β-configuration and each of R$^{12}$ and R$^{13}$ represents a hydrogen atom, or Ib) R$^{11}$ represents a hydrogen atom in the β-configuration and R$^{12}$ and R$^{13}$ together represent a second bond, or Ic) R$^{11}$ and R$^{12}$ together represent a second bond and R$^{13}$ represents a hydrogen atom, or Id) R$^{11}$ represents a hydrogen atom in the a-configuration and R$^{12}$ and R$^{13}$ together represent a second bond, and in Ia), Ib), Ic) or Id)

X represents an oxygen atom, the hydroxyimino grouping >N~OH or two hydrogen atoms, R$^1$ represents a hydrogen atom or a methyl group, R$^2$ represents a hydroxy group, a C$_1$–C$_{10}$-alkoxy group or a C$_1$–C$_{10}$-acyloxy group, R$^3$ represents a hydrogen atom; the grouping —(CH$_2$)$_n$CH$_2$Z wherein n is 0, 1, 2, 3, 4 or 5 and Z represents a hydrogen atom, a cyano group or the radical —OR$^5$ in which R$^5$=H, C$_1$–C$_{10}$-alkyl or C$_1$–C$_{10}$-acyl; the grouping —(CH$_2$)$_m$C≡C—Y wherein m is 0, 1 or 2 and Y represents a hydrogen, fluorine, chlorine, bromine or iodine atom, or a C$_1$–C$_{10}$-hydroxyalkyl, C$_1$–C$_{10}$-alkoxyalkyl or C$_1$–C$_{10}$-acyloxyalkyl radical; or the grouping —(CH$_2$)$_p$—CH=CH—(CH$_2$)$_k$CH$_2$R6 wherein p is 0 or 1 and k is 0, 1 or 2 and R$^6$ represents a hydrogen atom, a hydroxy group, a C$_1$–C$_4$-alkoxy radical or a C$_1$–C$_4$-acyloxy radical, wherein in Ia) and Ib) R$^2$ is in the α-configuration and R$^3$ is in the β-configuration and in Ic) and Id) R$^2$ is in the β-configuration and R$^3$ is in the α-configuration, or alternatively R$^2$ and R$^3$ together represent a radical of the formula

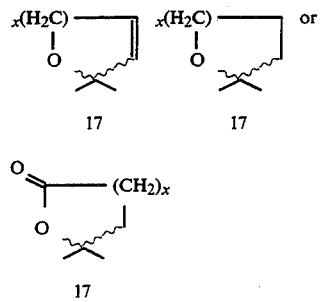

wherein x=1 or 2, R$^4$ represents a hydrogen atom; a cyano group; a chlorine, fluorine, bromine or iodine atom; a trialkylsilyl group; a trialkylstannyl group; a straight-chain or branched, saturated or unsaturated, C$_1$–C$_8$-alkyl, -acyl or alkoxyalkyl radical; an amino group

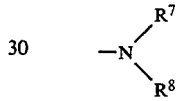

in which R$^7$ and R$^8$, each independently of the other, represents a hydrogen atom or a C$_1$–C$_4$-alkyl group; a corresponding amine oxide

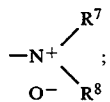

or the grouping —OR$^9$ or —S(O)$_i$R9 in which i =0, 1 or 2 and R$^9$ represents a hydrogen atom, a methyl, ethyl, propyl, isopropyl, methoxyphenyl, allyl or 2-dimethylaminoethyl group; or R$^4$ represents a heteroaryl radical of formula Iα

in which A represents a nitrogen, oxygen or sulphur atom, —B—D—E— represents the sequence of elements —C—C—C—, —N—C—C— or —C—N—C— and R$^{10}$ represents a hydrogen atom; a cyano group; a chlorine, fluorine, bromine or iodine atom; a trialkylsilyl group; a trialkylstannyl group; a straight-chain or branched, saturated or unsaturated C$_1$–C$_8$-alkyl, -acyl or alkoxyalkyl radical; an amino group

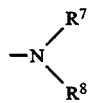

in which $R^7$ and $R^8$, each independently of the other, represents a hydrogen atom or a $C_1$–$C_4$-alkyl group; a corresponding amine oxide

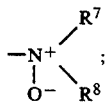

or the grouping —$OR^9$ or —$S(O)_iR^9$ in which i=0 1 or 2 and $R^9$ represents a hydrogen atom, a methyl, ethyl, propyl, isopropyl, methoxyphenyl, allyl or 2-dimethylaminoethyl group;

or $R^4$ represents a heteroaryl radical of formula Iβ

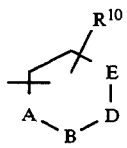

in which A represents a nitrogen atom and —B—D—E— represents the sequence of elements —C—C—C—, —N—C—C—, —C—N—C— or —C—C—N— and $R^{10}$ has the meaning already given, or $R^4$ represents a phenyl radical of formula Iγ

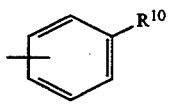

in which $R^{10}$ has the meaning already given,
and the pharmacologically tolerable addition salts thereof with acids.

2. A compound according to claim 1, wherein said compound is

17α-hydroxy-17β-(3-hydroxypropyl)-11β-[4-(3-pyridinyl)phenyl]-14β-oestr-4-en-3-one 11β-(4-acetylphenyl)-17α-hydroxy-17β-(3-hydroxypropyl)-14β-oestr-4-en-3-one 11β-[4-(3-furanyl)phenyl]-17α-hydroxy-17β-(3-hydroxypropyl)-14β-oestr-4-en-3-one 4'-[17α-hydroxy-17β-(3-hydroxypropyl)-3-oxo-14β-oestr-4-en-11β-yl][1,1'-biphenyl]-4-carbonitrile (Z)-11β-(4-acetylphenyl)-17α-hydroxy-17β-(3-hydroxy-1-propenyl)-14β-oestr-4-en-3-one (Z)-4'-[17α-hydroxy-17β-(3-hydroxy-1-propenyl)-3-oxo-14β-oestr-4-en-11β-yl][1,1'-biphenyl]-4-carbonitrile 11β-(4-acetylphenyl)-17α-hydroxy-17β-(methoxymethyl)-14β-oestr-4-en-3-one 11β-(4-acetylphenyl)-17α-hydroxy-3-oxo-14β-oestr-4-ene-17β-acetonitrile 11β-[4-(3-furanyl)phenyl]-17α-hydroxy-17β-(3-hydroxypropyl)-14β-oestra-4,15-dien-3-one 4'-[17α-hydroxy-17β-(3-hydroxypropyl)-3-oxo-14β-oestra-4,15-dien-11β-yl][1,1'-biphenyl]-4-carbonitrile 11β-(4-acetylphenyl)-17α-hydroxy-17β-methyl-14β-oestra-4,15-dien-3-one 17β-hydroxy-11β-(4-methoxyphenyl)-17α-methyloestra-5,14-dien-3-one 11β-[4-(3-furanyl)phenyl]-17β-hydroxy-17α-methyloestra-5,14-dien-3-one 11β-(4-acetylphenyl)-17β-hydroxy-17α-methyloestra-5,14-dien-3-one 11β-(4-acetylphenyl)-17β-hydroxy-17α-(3-hydroxypropyl)oestra-5,14-dien-3-one 4'-[17β-hydroxy-17α-(3-hydroxypropyl)-3-oxo-oestra-4,14-dien-11β-yl][1,1'-biphenyl]-4-carbonitrile 11β-(4-acetylphenyl)-17β-hydroxy-17α-(1-propynyl)oestra-4,14-dien-3-one 11β-(4-acetylphenyl)-4',5'-dihydrospiro[oestra-4,14-diene-17β,2'(3'H)-furan]-3-one 11β-[4-(3-furanyl)phenyl]-17β-hydroxy-17α-(3-hydroxypropyl)oestra-4,15-dien-3-one 4'-[17β-hydroxy-17α-(3-hydroxypropyl)-3-oxo-oestra-4,15-dien-11β-yl][1,1'-biphenyl]-4-carbonitrile 11β-[4-(3-furanyl)phenyl]-17β-hydroxy-17α-methyloestra-4,15-dien-3-one 11β-(4-acetylphenyl)-17β-hydroxy-3-oxo-oestra-4,15-diene-17α-acetonitrile 17-hydroxy-17α-methyl-11β-[4-(3-thienyl)phenyl]oestra-4,14-dien-3-one 17β-hydroxy-11β-(4-methoxyphenyl)-17α-methyloestra-4,15-dien-3-one 11β-(4-acetylphenyl)-17β-hydroxy-17α-methyoestra-4,15-dien-3-one 17β-hydroxy-17α-methyl-11β-[4-(3-pyridinyl)phenyl]oestra-4,15-dien-3-one 4'-[17β-hydroxy-17α-methyl-3-oxo-oestra-4,15-dien-11β-yl][1,1'-biphenyl]-4-carbonitrile 4'-[17β-methoxy-17α-methyl-3-oxo-oestra-4,15-dien-11β-yl][1,1'-biphenyl]-4-carbonitrile 17β-hydroxy-11β-(4-methoxyphenyl)-17α-(1-propynyl)oestra-4,15-dien-3-one 4'-[17β-hydroxy-17α-(1-propynyl)-3-oxo-oestra-4,15-dien-11β-yl][1,1'-biphenyl]-4-carbonitrile 11β-[4-(3-furanyl)phenyl]-17β-hydroxy-17α-(1-propynyl)oestra-4,15-dien-3-one 11β-(4-acetylphenyl)-17β-hydroxy-17α-(1-propynyl)oestra-4,15-dien-3-one 4'-[4',5'-dihydro-3-oxospiro[oestra-4,15-diene-17β,2'(3'H)-furan]-11β-yl][1,1'-biphenyl]-4-carbonitrile (Z)-17β-hydroxy-17α-3-hydroxy-1-propenyl)-11β-(4-methoxyphenyl)-oestra-4,15-dien-3-one 11β-(4-acetylphenyl)-17α-ethynyl-17β-hydroxyoestra-4,15-dien-3-one 4'-[17α-ethynyl-17β-hydroxy-3-oxo-oestra-4,15-dien-11β-yl][1,1'-biphenyl]-4-carbonitrile 11β-[4-(dimethylamino)phenyl]-17β-hydroxy-17α-methyloestra-4,15-dien-3-one.

3. A pharmaceutical composition comprising at least one compound of claim 1 and a pharmaceutical carrier.

* * * * *